United States Patent [19]

Hirano et al.

[11] Patent Number: 5,498,687

[45] Date of Patent: Mar. 12, 1996

[54] UNSATURATED IMIDE COMPOUNDS CONTAINING ALICYCLIC STRUCTURE, PROCESS FOR PRODUCING THE SAME AND INTERMEDIATE THEREFOR

[75] Inventors: Yasuhiro Hirano; Yasuhiro Endo; Kazuo Takebe; Mitsuhiro Shibata, all of Tsukuba; Shuichi Kanagawa, Tsuchiura; Yutaka Shiomi, Tsukuba; Masatsugu Akiba, Tsukuba; Shinichiro Kitayama, Tsukuba, all of Japan

[73] Assignee: Sumitomo Chemical Company, Limited, Osaka, Japan

[21] Appl. No.: 411,880

[22] Filed: Mar. 28, 1995

Related U.S. Application Data

[62] Division of Ser. No. 202,068, Feb. 25, 1994, Pat. No. 5,444,165, which is a division of Ser. No. 142,578, Oct. 28, 1993, Pat. No. 5,326,881.

[30] Foreign Application Priority Data

| Oct. 28, 1992 | [JP] | Japan | 4-290036 |
| Nov. 13, 1992 | [JP] | Japan | 4-303616 |
| Nov. 19, 1992 | [JP] | Japan | 4-310247 |
| May 24, 1993 | [JP] | Japan | 5-121136 |
| May 27, 1993 | [JP] | Japan | 5-125888 |

[51] Int. Cl.$^6$ ............................................. C08G 59/18
[52] U.S. Cl. .................................... 528/96; 528/170
[58] Field of Search ........................................ 528/96, 170

[56] References Cited

U.S. PATENT DOCUMENTS

| 2,444,536 | 7/1948 | Searle | 548/520 |
| 3,232,994 | 2/1966 | Hirano et al. | 548/520 |
| 4,130,564 | 12/1978 | Haug et al. | 548/520 |
| 4,460,783 | 7/1984 | Nishikawa et al. | 548/520 |
| 4,968,762 | 10/1990 | Yamaya et al. | 528/170 |
| 5,089,628 | 2/1992 | Maruta et al. | 548/520 |
| 5,106,937 | 4/1992 | Yamaya et al. | 528/170 |
| 5,149,761 | 9/1992 | Reuter et al. | 528/170 |

FOREIGN PATENT DOCUMENTS

| 032745 | 7/1981 | European Pat. Off. . |
| 192480 | 8/1986 | European Pat. Off. . |
| 2399412 | 3/1979 | France . |
| 2636626 | 3/1990 | France . |
| 57-159764 | 10/1982 | Japan . |

OTHER PUBLICATIONS

Murata et al; Chem. Abs., 113:190882m (1990).
Hayashi et al; Chem. Abs., 116:175693u (1992).
Murata et al; Chem. Abs., 116:204479m (1992).

*Primary Examiner*—Melvyn I. Marquis
*Assistant Examiner*—Margaret W. Glass
*Attorney, Agent, or Firm*—Cushman, Darby & Cushman

[57] ABSTRACT

An unsaturated imide compound represented by formula (1):

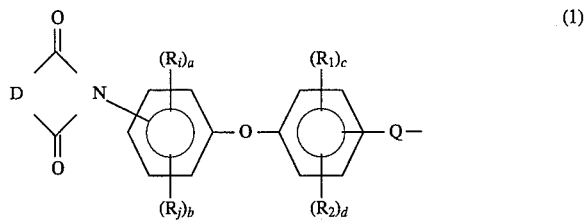

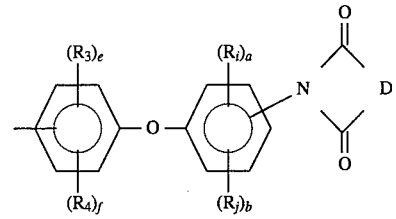

wherein Q is an alicyclic structure-containing hydrocarbon group having 4–20 carbon atoms; each of $R_1$, $R_2$, $R_3$, $R_4$, $R_i$ and $R_j$ represents a hydrogen atom, a halogen atom, a hydrocarbon group having 1–6 carbon atoms or a halogen-containing hydrocarbon group having 1–6 carbon atoms; each of a, b, c, d, e and f represents an integer of 0 to 4 satisfying $a+b \leq 4$, $c+d \leq 4$ and $e+f \leq 4$ and D represents a divalent organic group having 2–24 carbon atoms and an ethylenically unsaturated double bond, a process for producing the unsaturated imide compound of formula (1) and intermediates for producing the unsaturated imide compound of formula (1). The unsaturated imide compound of formula (1) is well soluble in organic solvents and can give cured products excellent in heat resistance, low water absorption and flexibility.

15 Claims, No Drawings

UNSATURATED IMIDE COMPOUNDS CONTAINING ALICYCLIC STRUCTURE, PROCESS FOR PRODUCING THE SAME AND INTERMEDIATE THEREFOR

This is a division of application No. 08/202,068, filed Feb. 25, 1994, now U.S. Pat. No. 5,444,165 which is a divisional of Ser. No. 08/142,578, filed Oct. 28, 1993, now U.S. Pat. No. 5,326,881.

BACKGROUND OF THE INVENTION

This invention relates to a novel unsaturated imide compound which is well soluble in an organic solvent and gives a cured product excellent in heat resistance, low water absorbability and flexibility; a process for producing the unsaturated imide compound; and an intermediate therefor.

A thermosetting resin composition comprising the above unsaturated imide compound as a main component can be used as a laminate, sealing material, insulating material, sliding material and other molding materials in the electric and electronic fields.

This invention is also concerned with a dinitro compound and a diamino compound which are intermediates for producing the above unsaturated imide compound.

Heretofore, electric and electronic parts such as semiconductor and the like have been sealed with an epoxy resin. This is because the sealing with an epoxy resin is more economically advantageous than hermetic seal system using glass, metal and ceramic. However, the recent trend is that the conditions for use of electronic parts become severe. For example, the fabrication method is now switching from insert fabrication to surface fabrication, and this is accompanied by a result that sealing materials per se are exposed to solder bath temperatures. Consequently, the sealing material is required to have excellent heat resistance; however, epoxy resins do not sufficiently satisfy the requirement for heat resistance.

Thermosetting polyimide resin-sealing has been proposed for the purpose of obtaining high heat resistance. For example, 4,4'-diphenylmethane bismaleimide has been known as a bismaleimide type thermosetting resin. The cured product of this compound is excellent in heat resistance, but is brittle and high in hygroscopicity. Also, this compound has a low solubility in general purpose organic solvents and it is difficult to prepare a varnish therefrom in the formation of a laminate or the like.

The known general method for preparing unsaturated imide compounds is a chemical ring-closure method which comprises reacting an aromatic amine solution with a solution of an acid anhydride such as maleic anhydride or the like, and then allowing a dehydrating agent to act thereon [U.S. Pat. No. 2,444,536; Org. Synth., 41, 93 (1961) and the like]. However, this method has a tendency that acetic acid, though in a slight amount, remains in the product and hence acetic acid odor becomes a problem when the product is cured at a high temperature. Impurities due to acetic acid tends to be produced under some conditions, whereby the purity of product is lowered. Many proposals have been made for solving this problem. A typical example thereof is a method comprising reacting an aromatic amine solution with a solution of an acid anhydride such as maleic anhydride or the like, and then heat-dehydrating the resulting amic acid solution to cause ring-closure (for example, Japanese Patent Kokoku No. 55-46,394, Japanese Patent Application Kokai No. 60-11,465 and the like). According to this method, no acetic acid is produced, and hence, there is no problem due to acetic acid. However, since unsaturated imide compounds which are thermosetting resins are exposed to high temperature during curing, there are such problems that a high molecular weight product and gel are produced depending upon the reaction conditions and the structure and reactivity of the imide, whereby the purity of product is lowered and the still is contaminated. When the reaction conditions are made mild for solving the above problems, the reaction time must be greatly prolonged.

SUMMARY OF THE INVENTION

It is an object of this invention is to provide a novel unsaturated imide compound whose solubility in general purpose organic solvent has been improved without adversely affecting the heat resistance of its cured product and which can give a cured product having improved low water absorbability and flexibility.

It is another object of this invention is to provide a process for producing an unsaturated imide compound having a high purity and general-purpose applicability in a simple step in a good efficiency.

It is a further object of this invention is to provide a thermosetting resin composition which can give a cured product excellent in moisture resistance, adhesiveness and heat resistance.

It is a still further object of this invention is to provide an electronic part sealed with the above thermosetting resin composition.

It is another object of this invention is to provide a diamino compound and dinitro compound which are intermediates for preparing the unsaturated imide compound.

Other objects and advantages of this invention will become apparent from the following description.

According to this invention, there is provided an unsaturated imide compound represented by formula (1):

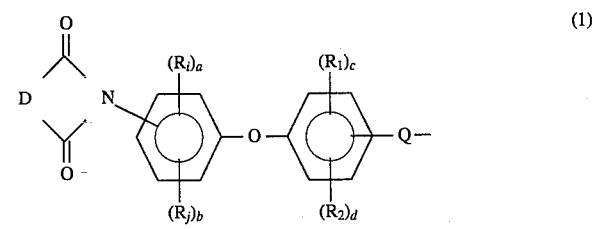

(1)

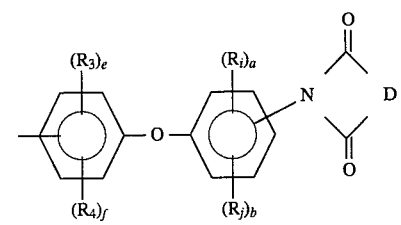

wherein Q represents an alicyclic structure-containing hydrocarbon group having 4–20 carbon atoms; each of $R_1$, $R_2$, $R_3$, $R_4$, $R_i$ and $R_j$ represents a hydrogen atom, a halogen atom, a hydrocarbon group having 1–6 carbon atoms or a halogen-containing hydrocarbon group having 1–6 carbon atoms; each of a, b, c, d, e and f represents an integer of 0–4 satisfying the conditions of $a+b \leq 4$, $c+d \leq 4$, and $e+f \leq 4$; and D represents a divalent organic group having 2–24 carbon atoms and an ethylenically unsaturated double bond.

This invention further provides a process for producing an unsaturated imide compound represented by formula (1) which comprises reacting an diamino compound represented by formula (2):

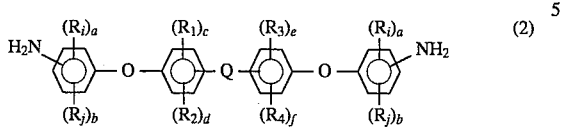 (2)

wherein Q, $R_1$, $R_2$, $R_3$, $R_4$, $R_i$ and $R_j$ are as defined in formula (1) and a, b, c, d, e and f are also as defined in formula (1), with an unsaturated dicarboxylic acid anhydride represented by formula (3):

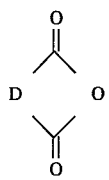 (3)

wherein D is as defined in formula (1), to synthesize an amic acid compound represented by formula (4):

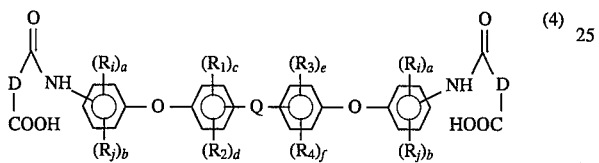 (4)

wherein Q, $R_1$, $R_2$, $R_3$, $R_4$, $R_i$, $R_j$, D, a, b, c, d, e and f are as defined in formula (1), and heating the amic acid compound in a non-protonic polar solvent in the presence of an acidic catalyst to cause hydration-ring-closure reaction (imidation). The dehydration-ring-closure reaction (imidation) of the amic acid compound may be effected in the presence of an acidic catalyst in two stages, in the first stage of which preliminary reaction is effected at a temperature of 60° C. to 120° C. while the water formed is removed by azeotropic dehydration and in the second stage, reaction is effected at a higher temperature than 120° C. while the water formed is removed by azeotropic dehydration.

This invention further provides a diamino compound represented by formula (2) mentioned above or a dinitro compound represented by formula (5), the two being intermediates for preparing the unsaturated imide compound of formula (1):

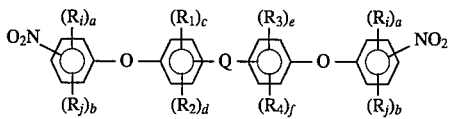 (5)

wherein Q, $R_1$, $R_2$, $R_3$, $R_4$ and $R_i$, $R_j$ a, b, c, d, e and f are as defined in formula (1).

This invention further provides a thermosetting resin composition comprising the unsaturated imide compound of formula (1) and a curing accelerator.

DETAILED DESCRIPTION OF THE INVENTION

The alicyclic structure-containing unsaturated imide compound of formula (1) is excellent in solubility in general-purpose organic solvents, and the cured product of the unsaturated imide compound is excellent in heat resistance, low water-absorbability, flexibility and the like.

The diamino compound represented by formula (2) and the dinitro compound represented by formula (5) are novel and useful as intermediates for preparing the unsaturated imide compound of formula (1).

The diamino compound of formula (2) is also useful as a curing agent for the unsaturated imide compound of formula (1). The diamino compound of formula (2) is excellent in solubility in general purpose organic solvents, and hence, when it is used as a curing agent for the unsaturated imide compound of formula (1) or as a starting material for preparing the imide compound of formula (1), the processability and workability are improved. Also, when it is used as a curing agent for the unsaturated imide compound of formula (1), a cured product having excellent heat resistance, toughness and low water-absorbability can be obtained.

The production process of this invention has the following advantages:

(A) The unsaturated imide compound can be produced with a high purity in a simple step in a good efficiency.

(B) The catalyst, solvent and washing liquid used can be separated and reused, and hence, the process is very advantageous in economy.

(C) The total amount of the solvent used in the crystallization step is relatively small, and hence, can be controlled to that within the capacity of the apparatus used in the reaction. Therefore, the process does not require a separate large apparatus for pelletization which is usually required, and the recovery of the solvent used can be effected in a short time.

(D) A series of the reactions including from the reaction for obtaining a dinitro compound from a nitrobenzene derivative and a bisphenol to the reaction for obtaining the final unsaturated imide compound can be conducted without isolating or purifying intermediate products, and hence, the time, apparatus, labor and the like required for the isolation and purification can be saved.

In addition, when the imidation is effected in two stages, it is possible to shorten the reaction time, reduce the amount of the high molecular weight product and produce a highly pure product.

The thermosetting resin composition of this invention may contain an epoxy resin and an epoxy resin curing agent. The thermosetting resin composition is excellent in processability and the cured product thereof is excellent in heat resistance, particularly strength and adhesiveness at high temperatures. Thus, the thermosetting resin composition is useful as a laminate, sealing material, insulating material, sliding material or other molding materials in the electric and electronic fields. In particular, since the thermosetting resin composition is superior in moisture resistance to the conventional thermosetting resins, it is very useful as an sealing material for electric and electronic parts. The electronic parts sealed with the thermosetting resin composition of this invention is excellent in heat resistance, moisture resistance and solder cracking resistance.

In formula (1) for the imide compound, Q represents an alicyclic structure-containing divalent hydrocarbon group having 4–20 carbon atoms and typical examples thereof include groups represented by the following formulas (a) to ( f), and groups of formulas (a), (b) and (c) are preferable:

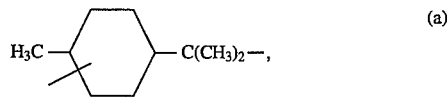 (a)

-continued (b) H₃C—⟨cyclohexyl⟩—CH(CH₃)₂

(c) [bicyclic structure]

(d) [bicyclic structure]

(e) [bicyclic structure]

(f) [bicyclic structure]

In formula (1), each of $R_1$, $R_2$, $R_3$, $R_4$, $R_i$ and $R_j$ represents a hydrogen atom, a halogen atom, a hydrocarbon group having 1–6 carbon atoms or a halogen-containing hydrocarbon group having 1–6 carbon atoms. The hydrocarbon group having 1–6 carbon atoms includes straight or branched chain alkyl groups such as methyl, ethyl, propyl, butyl, amyl and hexyl; cycloalkyl groups having 3–6 carbon atoms such as cyclohexyl group and the like; and phenyl group. The halogen-containing hydrocarbon group having 1–6 carbon atoms includes the above-mentioned alkyl groups having 1–6 carbon atoms whose at least one hydrogen atom has been substituted by a halogen atom. The halogen atom includes fluorine, chlorine, bromine and iodine.

In formula (1), D represents a divalent organic group having 2–24 carbon atoms and an ethylenically unsaturated double bond, and typical examples thereof include —CH=CH— (g), CH₂=CH—CH₂— (h), —C(CH₃)=CH— (i) and —C(Cl)=C(Cl)— (j).

In formula (2) for the diamino compound, Q, $R_1$, $R_2$, $R_3$, $R_4$, $R_i$ and $R_j$ are as explained above as to formula (1), and the diamino compound represented by formula (2) includes bis[4-(4-aminophenoxy)phenyl]menthane, bis[2-(4-aminophenoxy)phenyl]menthane, 1-[2-(4-aminophenoxy)phenyl]-8-[4-(4-aminophenoxy)phenyl]menthane, bis[4-(3-aminophenoxy)phenyl]menthane, bis[2-(3-aminophenoxy)phenyl]menthane, 1-[2-(3-aminophenoxy)phenyl]-8-[4-(3-aminophenoxy)phenyl]menthane, bis[4-(4-aminophenoxy)-3-methylphenyl)menthane, bis[4-(4-aminophenoxy)-3,5-dimethylphenyl]menthane, bis[4-(4-aminophenoxy)-3-butyl-6-methylphenyl]menthane, bis[4-(4-amino-5-methylphenoxy)-3-methylphenyl]menthane, bis[4-(4-amino-5-methylphenoxy)-3,5-dimethylphenyl]menthane, bis[4-(4-amino-5-methylphenoxy)-3-butyl-6-methylphenyl] menthane, bis[2-(4-aminophenoxy)-3-methylphenyl]menthane, 1-[2-(4-aminophenoxy)-3-methylphenyl]-8-[4-(4-aminophenoxy)-3-methylphenyl]methane, bis[4-(4-aminophenoxyphenyl]dicyclopentane, bis[2-(4-aminophenoxy)phenyl]-dicyclopentane, [2-(4-aminophenoxy)phenyl]-[4-(4-aminophenoxy)phenyl]dicyclopentane, bis[4-(3-aminophenoxy)phenyl]dicyclopentane, bis[2-(3-aminophenoxy)phenyl]dicyclopentane, [2-(3-aminophenoxy)phenyl]-[4-(3-aminophenoxy)phenyl]dicyclopentane, bis[4-(4-aminophenoxy)-3-methylphenyl]dicyclopentane, bis[4-(4-aminophenoxy)-3,5-dimethylphenyl]dicyclopentane, bis[4-(4-aminophenoxy)-3-butyl-6-methylphenyl]dicyclopentane, bis[4-(4-amino-5-methylphenoxy)-3-methylphenyl]dicyclopentane, bis[4-(4-amino-5-methylphenoxy)-3,5-dimethylphenyl]dicyclopentane, bis[4-(4-amino-5-methylphenoxy)-3-butyl-6-methylphenyl]dicyclopentane, bis[2-(4-aminophenoxy)-3-methylphenyl]dicyclopentane, [2-(4-aminophenoxy)-3-methylphenyl]-[4-(4-aminophenoxy)-3-methylphenyl]dicyclopentane and the like.

The unsaturated dicarboxylic acid anhydride represented by formula (3) includes, for example, maleic anhydride, itaconic anhydride, citraconic anhydride, dichloromaleic anhydride, pyrocinchonic anhydride, tetrahydrophthalic anhydride and the like; Diels-Alder reaction products of these unsaturated dicarboxylic acid anhydrides with dienes such as cyclization, addition products of cyclopentadiene, furan or terpinene with maleic anhydride, and these compounds may be used alone or in admixture of two or more.

The unsaturated imide compound of formula (1) can be produced by a process comprising preparing an amic acid compound of formula (4) from a diamino compound of formula (2) and an unsaturated dicarboxylic acid anhydride of formula (3), and then subjecting the amic acid compound to dehydration-ring-closure reaction by heating in the presence of a catalyst.

The preparation of the amic acid compound of formula (4) is carried out by contacting an organic solvent solution of the unsaturated dicarboxylic acid anhydride of formula (3) with a solution of the diamino compound of formula (2). In this case, the unsaturated dicarboxylic acid anhydride is preferably used in a proportion of 1–1.5 equivalents per equivalent of the amino group of the diamino compound. When it is less than 1 equivalent, some amino groups remain without being converted to amic acid, and the use of more than 1.5 equivalents of the unsaturated dicarboxylic acid anhydride is insignificant and rather undesirable because unreacted unsaturated carboxylic acids become left in the product. Usually, the diamino compound solution is continuously or in portions added to the organic solvent solution of the unsaturated dicarboxylic acid anhydride. The time required for the addition may be such that the formation of by-products is not remarkable though this is not critical, and usually, it is about 0.5–6 hours. The reaction temperature may be in the range of −20° C. to 120° C., preferably room temperature to 60° C. When the temperature is too low the reaction is too slow, and when the temperature is too high by-products such as polymers and the like are produced to lower the purity of the objective compound.

The solvent for dissolving the unsaturated dicarboxylic acid anhydride of formula (3) includes non-protonic polar solvents such as dimethylformamide, dimethylsulfoxide, dimethylacetamide, 1-methyl-2-pyrrolidone, sulfolane, 1,3-dimethyl-2-imidazolidinone and the like; aliphatic and alicyclic hydrocarbons such as hexane, heptane, decane, cyclohexane and the like; aromatic hydrocarbons such as toluene, xylene and the like; and halogenated hydrocarbons such as 1,2-dichloroethane, chlorobenzene and the like. These may be used alone or in admixture of two or more.

The total amount of the solvents used is 1–10 times the total weight of the unsaturated dicarboxylic acid anhydride and the diamino compound, and preferably 1–5 times in view of the yield per one reaction. The reaction is completed in about 0.5–4 hours after completion of the addition of the diamino compound, upon which the amic acid of formula (4) is obtained.

Subsequently, the ring-closure reaction is conducted to produce the unsaturated imide compound of formula (1).

The non-protonic polar solvent may be basically the same as used in the formation of the amic acid, and includes oxygen-containing and nitrogen-containing solvents such as dimethylformamide, dimethylsulfoxide, dimethylacetamide, 1-methyl-2-pyrrolidone, sulfolane, 1,3-dimethyl-2-imidazolidinone and the like and mixtures thereof.

Since dehydration-ring-closure is caused during the imidation reaction, water is formed. In order to take the water out of the system, it is preferable to effect azeotropic dehydration using at least one solvent which can be azeotropically distilled with water such as an aliphatic or alicyclic hydrocarbon, for example, hexane, heptane, decane, cyclohexane or the like; an aromatic hydrocarbon, for example, toluene, xylene or the like; or a halogenated hydrocarbon, for example, 1,2-dichloroethane, chlorobenzene or the like. The amount of the solvent used for the azeotropic dehydration is 1 to 20 times, preferably 2 to 10 times the weight of the amic acid compound.

The acidic catalyst used for the ring-closure of the amic acid compound includes mineral acids such as sulfuric acid, hydrochloric acid, phosphoric acid, polyphosphoric acid and the like; organic sulfonic acids such as p-toluenesulfonic acid, methanesulfonic acid and the like; halogenated carboxylic acids such as trichloro-acetic acid, trifluoroacetic acid and the like; cationic ion-exchange resins; heteropoly-acids such as phosphotungstic acid, phosphomolybdic acid and the like; solid acids such as silica-alumina and the like. Among them, sulfuric acid, p-toluenesulfonic acid and sulfonic acid-form ion-exchange resin are preferred. When a heteropoly-acid is used, it is preferable to previously treat the catalyst at 150°–200° C. to enhance the activity. The above acids maybe supported on a carrier such as active carbon, silica gel, silicaalumina, inorganic salt or in the form of a salt with an diamino compound. The amount of the acidic catalyst used is varied depending upon the kind thereof, and is 0.1 to 10% by weight based on the total weight of the starting diamino compound and unsaturated dicarboxylic acid anhydride in the case of a homogeneous system (the system from which the catalyst cannot be separated by filtration) or 5 to 100% by weight based on the total weight of the starting diamino compound and unsaturated dicarboxylic acid anhydride in the case of a heterogeneous system (the system from which the catalyst can be separated by filtration). When the amount is smaller than the above range, the desired catalytic effect is not obtained, and even if the catalyst is used in a larger amount than the above range, no better effect is obtained and rather the operation for separating the catalyst becomes complicated. The heterogenous catalyst can be used as it is or after subjecting it to known regeneration treatment depending upon the characteristics of the catalyst.

The reaction temperature may be varied depending upon the properties of the objective unsaturated imide compound, and is preferably 80°–160° C., more preferably 100-150° C., under reflux. The reaction time is preferably 0.5 to 20 hours, more preferably 2 to 15 hours. The reaction pressure may be at atmospheric pressure, under reduced pressure or under pressure, and is adequately determined depending upon the kind of solvent, the necessary temperature and the like. The reaction is effected while the water formed by ring-closure is separated and taken out of the system by use of an apparatus such as a Dean-Stark azeotropic dehydration tube or the like.

The above reaction (imidation reaction) may be effected in the following two stages. In the first stage, preliminary ring-closure reaction is effected in a solvent. The solvent may be the same as used in the formation of the amic acid. The temperature for the preliminary reaction is preferably 60° to 120° C., more preferably 80° to 110° C., under reduced pressure under reflux. The reaction time is preferably 0.1 to 4 hours, more preferably 0.5 to 2 hours. During the reaction, the water formed by the ring-closure is separated and taken out of the system by use of an apparatus such as the Dean-Stark azeotropic dehydration tube or the like.

After the preliminary ring-closure reaction, the main reaction is effected in the second stage. While azeotropic dehydration is effected the pressure is slowly returned to atmospheric pressure from the reduced pressure and the temperature is elevated to a higher temperature than 120° C., and the azeotropic dehydration is continued. The reaction temperature is preferably higher than 120° C. and not more than 200° C., more preferably more than 120° C. and not higher than 160° C. When the temperature is 120° C. or lower, the ring-closure reaction time cannot be significantly shortened, and when it is higher than 200° C. polymerization of the unsaturated imide compound is caused and hence a product having a sufficiently high purity cannot be obtained. The reaction time is preferably about 1–6 hours.

After the reaction, the solvent for azeotropic distillation is removed by distillation under reduced pressure and the non-protonic polar solvent is subsequently removed by distillation under reduced pressure. The reaction may be effected while the solvent is removed by distillation. In this case, it is preferable to remove 70% or more, more preferably 80% or more, of the solvent by distillation. The larger the proportion of the solvent removed, the lower the cost for removing by distillation the non-protonic polar solvent remaining in the product from the solvent used in the crystallization of product (this is explained herein-after) becomes. When the proportion of the solvent removed by distillation is less than 70%, the product tends to be dissolved in the solvent when the crystallization mentioned below is effected, and hence, the recovery of the product is reduced.

The concentrate thus obtained is contacted, as it is or after being dispersed or dissolved in an organic solvent, with a poor solvent, whereby the unsaturated imide compound in the reaction mixture can be crystallized. When the solubility of the unsaturated imide compound in the organic solvent used is too large, it becomes difficult to crystallize the product, and when it is too small, it becomes necessary to use a large amount of an organic solvent for the dissolution. Hence, it is necessary to select a solvent capable of adequately dissolving the alicyclic structure-containing unsaturated imide compound. For this requirement, ether solvents and glycol solvents are preferable, and methyl Cellosolve and propylene glycol monomethyl ether are particularly preferable.

As the poor solvent, alcohol solvents such as methanol, ethanol, propanol and the like; and water are preferred.

If necessary, the non-protonic polar solvent may be extracted from the concentrate of the reaction product by a method comprising adding an alcohol solvent such as methanol, ethanol, 1-propanol, 2-propanol, 1-butanol, 2-butanol or the like to the concentrate of the reaction product, heating the resulting mixture at a temperature of 40° to 150° C. with stirring, cooling the same, and then separating the alcohol layer. The amount of the alcohol solvent used is preferably 0.1 to 10 times, more preferably 0.5 to 3 times, the weight of the concentrate.

When the objective product is solidified in the solvent-recovery step subsequent to the imidation reaction or when the product is not easily taken out of the reaction vessel after the extraction with an alcohol solvent because the product does not become well-dispersible crystals, the product may be formed into a powder by adding the solvent thereto in an amount of 0.1 to 4 times, preferably 0.5 to 3 times the weight of the product to dissolve, disperse or suspend the product in the solvent and then contacting the resulting solution, dispersion or suspension with a poor solvent in an amount of 1 to 20 times the weight of the product.

The solvent used includes ketones such as acetone, methyl ethyl ketone and the like; nitriles such as acetonitrile and the like; acyclic ethers such as diethyl ether, methyl t-butyl ether and the like; cyclic esters such as tetrahydrofuran, 1,4-dioxane and the like; glycol ethers such as methyl Cellosolve, ethyl Cellosolve, propylene glycol monomethyl ether and the like. Methyl Cellosolve, propylene glycol monomethyl ether and the like are preferred because the product is uniformly dispersed therein. Specific examples of the poor solvent include water, methanol, ethanol, 2-propanol, 1-propanol, 1-butanol, 2-butanol and the like.

The objective unsaturated imide compound of formula (1) is obtained by filtering the crystals of the unsaturated imide compound obtained by the above-mentioned operation, washing the crystals with water, 2-propanol, methanol or the like and then drying the same by warming under reduced pressure. The product thus obtained has a sufficient purity as the starting material in industry; however, if necessary, the product may be recrystallized from an organic solvent such as an alcohol or the like.

It is also possible to obtain the unsaturated imide compound in the molten form by adding a suitable solvent to the concentrate of the reaction product to dissolve the concentrate, washing the resulting solution and then removing the organic solvent by distillation.

Specific examples of the organic solvent include ketone solvents such as methyl isobutyl ketone and the like; ester solvents such as ethyl acetate and the like; and hydrocarbon solvents such as toluene, xylene and the like. Among them, ketone solvents such as methyl isobutyl ketone and the like are preferred. The amount of the solvent used may be varied depending upon the solubility of the unsaturated imide compound in the solvent, and is preferably 2–20 times the expected weight of the unsaturated imide compound.

The washing is effected preferably by repeating mixing with water at 20°–90° C. and liquid separation at least two times. The water to be used may be tap water, industrial water, deionized water or an aqueous sodium chloride solution. It is preferable to add a weak base such as sodium bicarbonate or the like to the washing water to neutralize and remove the acidic catalyst. The pH of the aqueous layer is 4–8, preferably 5–7. The amount of the washing water is 0.5–20 times the weight of the unsaturated imide compound.

After the water washing, the water content in the solution is removed by an operation such as azeotropic dehydration or the like, and thereafter, if necessary, the inorganic components are removed by filtration. In this case, Celite and a filter aid such as ion-adsorber or the like may be used. The removal of the organic solvent by distillation is effected under reduced pressure or at atmospheric pressure to reduce the amount of the remaining solvent to 1% by weight or less based on the weight of the product. The product is taken out by heating the unsaturated imide compound to a melting or softening point or higher, withdrawing the molten product from the apparatus, and then cooling the same. According to this method, the product is obtained in the flake form.

The diamino compound of formula (2) used as one of the starting materials in the production of the unsaturated imido compound of formula (1) is a novel compound and can be prepared by reducing a dinitro compound represented by formula (5). The reaction mixture obtained by the reduction may be applied as such without isolating the diamino compound to the reaction with an unsaturated dicarboxylic acid anhydride of formula (3).

The dinitro compound of formula (5) is a novel compound and can be prepared by reacting a bisphenol of formula (6):

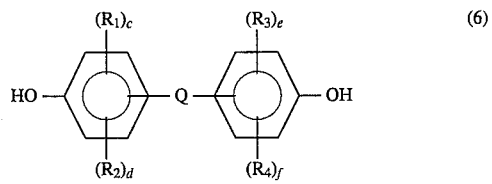

wherein Q, $R_1$, $R_2$, $R_3$, $R_4$, c, d, e and f are as defined in formula (1), with a nitrobenzene of formula (7):

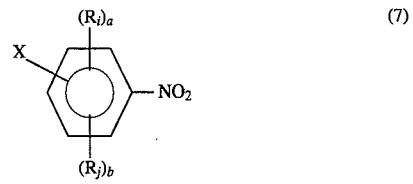

wherein X represents a halogen atom or a nitro group and Ri, Rj, a and b are as defined in formula (1), in the presence of a basic compound in a non-protonic polar solvent in the conventional manner as described in, for example, Org. Synth., 445 (Vol. II), U.S. Pat. No. 4,538,006, J. Org. Chem., 50 (20), 3717 (1985), J. Org. Chem., 50 (17), 3091 (1985), Japanese Patent Application Kokai Nos. 61-194,055 and 62-70,347, Macromolecules, 25, 64 (1992) and the like. The reaction mixture obtained by the above reaction may be subjected as such without isolating the dinitro compound to reduction to prepare the diamino compound.

The bisphenol of formula (6) and the nitrobenzene derivative of formula (7) which are the starting materials for preparing the dinitro compound of formula (5) have the respective isomers, and these isomers may be used alone or in admixture of two or more.

The nitrobenzene derivative of formula (7) includes p-fluoronitrobenzene, p-chloronitrobenzene, p-bromochloronitrobenzene, p-iodonitrobenzene, m-dinitrobenzene, o-chloronitrobenzene and the like, and p-chloronitrobenzene and m-dinitrobenzene are preferred. The nitrobenzene derivative is preferably used in an amount of 0.8 to 1.4 moles, more preferably 0.9 to 1.1 mole, per mole of the hydroxyl group of the bisphenol of formula (6). When the amount is more than 1.4 moles, the unreacted nitrobenzene derivative tends to remain in the product. When the amount is too small, the proportion of the unreacted hydroxyl group is increased and the hygroscopicity of the product is also increased.

The bisphenol of formula (6) is obtained by reacting a phenol with a hydrocarbon having an alicyclic structure having a divalent reactive site [see, for example, Chemich Berichte, 57, 854 (1924) and the like]. The reaction of an alicyclic structure-containing hydrocarbon such as dicyclopentadiene or the like or a terpene compound such as dipentene or the like with a phenol such as phenol, cresol, xylenol or the like in the presence of a catalyst such as boron trifluoride, boron trifluoride-ether complex or the like is a kind of Friedel-Crafts reaction, and is a known procedure [see, for example, UK Patent 1,043,159 (1963); Dutch Patent No. 6513720 (1967); Japanese Patent Kokai No. 4-139,142 and the like].

The Friedel-Crafts reaction of a phenol with an olefin is known to proceed in the presence of an acidic ion-exchange resin as a catalyst [see, for example, Reagents for Organic Synthesis, 513 (1967)]. The bisphenols used in this invention can be prepared by these known methods.

The starting phenols for preparing the bisphenol of formula (6) include phenol, cresol, xylenol, trimethylphenol, ethylphenol, propylphenol, butylphenol, amylphenol, hexylphenol, methylpropylphenol, methylbutyl-phenol, methylhexylphenol, chlorophenol, chlorocresol, chloroxylenol, bromophenol, bromocresol, bromoxylenol and the like, and phenol, cresol, xylenol and methylbutyl-phenol are preferred.

The hydrocarbon containing an alicyclic structure corresponding to the Q portion of formula (6) include cyclic dienes such as cyclopentadiene, cyclohexadiene and the like; terpenes such as dipentene, limonene, terpinolene, terpinene, menthadiene and the like; polycyclic structure dienes such as tetrahydroindene, dicyclopentadiene, norbornanediene, tricyclopentadiene and the like; etc., and of these, limonene, dipentene and dicyclopentadiene are preferred.

Usually, the Friedel-Crafts reaction is effected with a catalyst in an organic solvent at a temperature of −10° to 180° C. The catalyst used may be a Bronsted acid such as hydrochloric acid, sulfuric acid, hydrofluoric acid, phosphoric acid, paratoluenesulfonic acid or the like; a Lewis acid such as aluminum chloride, zinc chloride, iron (III) chloride, tin (IV) chloride, titanium tetrachloride, boron trifluoride, boron trifluoride-ether complex or the like; an ion-exchange resin such as Amberlite, Amberlist (these are trade names of Rohm & Haas) or the like. In view of the production of by-products and the yield, Lewis acids such as zinc chloride, iron (III) chloride, tin (IV) chloride, titanium tetrachloride, boron trichloride, boron trifluoride-ether complex and the like are preferred. The reaction solvent includes toluene, xylene and the like. The reaction, however, can be effected in the absence of the solvent. The phenols are used in excess of, preferably 2 moles or more per mole of, the alicyclic structure-containing hydrocarbon. After the reaction, the unreacted reactants remaining in the system are removed in a manner such as steam distillation, introduction of nitrogen under reduced pressure, thin film distillation or the like to obtain the bisphenol of formula (6). The bisphenol may contain an oligomer composed of the phenol and the alicyclic structure-containing hydrocarbon. If it is necessary to lower the viscosity of the unsaturated imide compound, the higher the purity of the bisphenol component, the better, and hence, the bisphenol recrystallized from a solvent such as toluene or the like is used.

The basic compound used in the reaction of the bisphenol with the nitrobenzene derivative includes alkali metal hydroxides such as sodium hydroxide, potassium hydroxide and the like; alkali metal carbonates, such as sodium carbonate, potassium carbonate and the like; alkali metal hydrogencarbonates such as sodium hydrogencarbonate, potassium hydrogencarbonate and the like; alkali metal alkoxides such as sodium methylate, potassium t-butoxide and the like; alkali metal hydrides such as lithium hydride, sodium hydride and the like; etc. These basic compounds may be used alone or in admixture of two or more. When a dinitrobenzene is used as the nitrobenzene derivative, it is preferable in view of safety such as avoidance of explosion or the like to use a weakly basic compound such as an alkali metal carbonate, for example, sodium carbonate, potassium carbonate or the like; or an alkali metal hydrogencarbonate such as sodium hydrogencarbonate, potassium hydrogencarbonate or the like.

It is possible to use a known catalyst for the coupling reaction. Active copper powder or a copper salt prepared by the method stated in, for example, Org. Synth., 445 (Vol. II) can be used. There may also be used a quaternary ammonium salt; a quaternary phosphonium salt; a cyclic or acyclic polyether such as a crown ether, polyethylene glycol or the like; or a terminal alkyl ether of the polyether; a nitrogen-containing cyclic or acyclic polyether; a terminal alkyl ether of the nitrogen-containing cyclic or acyclic polyether; or the like. These compounds may be used alone or in admixture of two or more. The solvent used includes non-protonic polar solvents such as dimethylformamide, dimethylsulfoxide, dimethylacetamide, 1-methyl-2-pyrrolidone, sulfolane, 1,3-dimethyl-2-imidazolidinone and the like. The amount of the solvent used is not critical; however, the solvent is preferably used in an amount 1 to 10 times the total weight of the starting materials. When water is produced during the reaction, a hydrocarbon or a halogenated hydrocarbon such as toluene, xylene, chlorobenzene or the like which can be azeotropically distilled with water may be added to effect azeotropic dehydration in order to remove the water formed from the system.

The starting materials may previously be charged into a reactor all at one time, or only the basic component may be finally added in small portions, or alternatively, a phenolate is previously prepared and then the nitrobenzene derivative is added gradually, which methods are typical. The coupling reaction is generally continued at a constant temperature between 50° C. and 200° C. or while the temperature is elevated step-by-step between these temperatures, until the reaction is completed. After the completion of the reaction, the salt formed is removed by filtration. A mixture (solution) containing the dinitro compound of formula (5) is produced by the above procedure. The dinitro compound may be isolated, or the mixture may be as such applied to the subsequent step without being subjected to isolation, the latter being preferred because the cost necessary for the isolation is saved.

The reduction reaction of the dinitro compound of formula (5) into the diamino compound of formula (2) is effected with hydrogen in the presence of a catalyst. When the dinitro compound is used without being isolated as mentioned above, the solution may, if necessary, be concentrated before the reaction. The reaction may be effected in the state that the dinitro compound is completely dissolved in a non-protonic solvent or the dinitro compound is not completely dissolved but suspended in the solvent. Usually, the solvent is used in an amount of 1–30 times the weight of the dinitro compound.

The catalyst used may be a metal such as palladium, nickel, platinum, cobalt, rhodium, ruthenium, copper or the like, a metal-supported catalyst or a Raney nickel catalyst, and the catalyst is used in an amount of 0.0005–20% by weight, preferably 0.01–5% by weight, in terms of metal, based on the weight of the dinitro compound. The catalyst may be previously suspended in a solvent, or may be gradually added to the reaction system with the progress of the reaction. Alternatively, the reaction may be effected by suspending the catalyst in a non-protonic solvent under a hydrogen atmosphere and dropwise adding thereto a suspension or solution of the dinitro compound. The carrier for supporting the catalyst includes active carbon, metal oxide, metal carbonate, metal sulfate and the like, and specific examples thereof are Celite, Floridil, alumina, silica gel, silica-alumina, magnesium oxide, zirconium oxide, barium sulfate, magnesium carbonate, barium carbonate and the like. Since the starting nitrobenzene derivative (contains a halogen atom) remains in the dinitro compound produced, there is a possibility of the derivative being reduced to generate a hydrogen halide, whereby the catalyst is deactivated. In this case, in order to prevent the deactivation, it is preferable that a base such as potassium carbonate, sodium carbonate or the like is added and the reaction is effected under alkaline conditions. Also, if necessary, an amine such as triethylamine or the like or a nitrogen-containing aromatic compound such as quinoline, isoquinoline or the like can be added in a proportion of 1 ppm to 1% by weight based on the weight of the solvent for controlling the reaction. The reaction is preferably carried out at a temperature of 0°–200° C. and a pressure of atmospheric pressure to 25 atms, preferably at a temperature of 0°–150° C. and a pressure of from atmospheric pressure to 10 atms. The reaction time is usually about 4–24 hours.

After the reaction, the catalyst is removed by filtration. The catalyst used may be reused as it is or after being subjected to regeneration treatment. The water formed by the reaction is removed by distilling the reaction mixture or by adding to the reaction mixture a solvent which can be azeotropically distilled with water and subjecting the resulting mixture to azeotropic dehydration. The above-mentioned operation makes it possible to obtain a mixture (solution) containing the diamino compound of formula (2). In this case, the diamino compound may be isolated from the mixture, or alternatively, the mixture may be as such applied to the subsequent step without being subjected to isolation of the diamino compound, and the latter is preferred because the cost for the isolation can be saved.

As already mentioned above, the diamino compound of formula (2) is reacted with the unsaturated dicarboxylic acid anhydride of formula (3) to prepare the unsaturated imide compound of formula (1).

The thermosetting resin composition of this invention comprises the unsaturated imide compound of formula (1) and a curing accelerator. The curing accelerator includes organic phosphine compounds such as triphenylphosphine, tri-4-methylphenylphosphine, tri-4-methoxyphenylphosphine, tributylphosphine, trioctylphosphine, tri-2-cyanoethylphosphine and the like; tertiary amines such as tributylamine, triethylamine, 1,8-diazabicyclo(5,4,0)undecene-7, triamylamine and the like; quaternary ammonium salts such as benzyltrimethylammonium chloride, benzyltrimethylammonium hydroxide, triethylammonium tetraphenylborate and the like; imidazoles; boron trifluoride complexes; transition metal acetylacetonates; and radical initiators such as benzoyl peroxide, di-t-butyl peroxide, dicumyl peroxide, lauroyl peroxide, acetyl peroxide, methyl ethyl ketone peroxide, cyclohexanone peroxide, t-butyl hydroperoxide, azobisisobutyronitrile and the like. However, the curing accelerator is not limited to them. Among them, organic phosphine compounds, 1,8-diazabicyclo(5,4,0)-undecene-7 and triethylammonium tetraphenylborate are particularly preferable in view of moisture resistance and curability.

In order to control the curing rate of the composition of this invention, it is possible to use a known polymerization inhibitor together with the above-mentioned curing accelerator. The polymerization inhibitor includes phenols such as 2,6-di-t-butyl-4-methylphenol, 2,2'-methylenebis(4-ethyl-6-t-butylphenol), 4,4'-methylenebis(2,6-di-t-butylphenol), 4,4'-thiobis(3-methyl-6-t-butylphenol), hydroquinone monomethyl ether and the like; polyhydric phenols such as hydroquinone, catechol, p-t-butylcatechol, 2,5-di-t-butylhydroquinone, methylhydroquinone, t-butylhydroquinone, pyrogallol and the like; phenothiazine compounds such as phenothiazine, benzophenothiazine, acetamidophenothiazine and the like; and N-nitrosoamine compounds such as N-nitrosodiphenyl-amine, N-nitrosodimethylamine and the like.

The thermosetting resin composition of this invention may contain an epoxy resin and an epoxy resin curing agent. The epoxy resin may be a known epoxy resin, including specifically novolak type epoxy resins derived from novolak resins which are reaction products of phenols such as phenol, o-cresol and the like with formaldehyde; glycidyl ether compounds derived from trihydric or more hydric phenols such as phloroglucin, tris(4-hydroxyphenyl)methane, 1,1,2,2-tetrakis(4-hydroxyphenyl)ethane and the like; glycidyl ether compounds derived from dihydric phenols, for example, bisphenol A, bisphenol F, hydroquinone, resorcin and 1,1'-bis(3-t-butyl-6-methyl-4-hydroxyphenyl)butane, tetramethylbiphenol and the like; diglycidyl ether compounds derived from halogenated bisphenols, for example, tetrabromobisphenol A and the like; glycidyl ether compounds of polyhydric phenols obtained by condensation of a phenol with an aromatic carbonyl compound; amine type epoxy resins derived from p-aminophenol, m-aminophenol, 4-aminometacresol, 6-aminometacresol, 4,4'-diaminodiphenylmethane, 3,3'-diaminodiphenymethane, 4,4'-diaminodiphenyl ether, 3,4'-diaminodiphenyl ether, 1,4-bis(4-aminophenoxy)benzene, 1,4-bis(3-aminophenoxy)benzene, 1,3-bis(4-aminophenoxy)benzene, 1,3-bis(3-aminophenoxy)benzene, 2,2-bis(4-aminophenoxyphenyl)propane, p-phenylenediamine, m-phenylenediamine, 2,4-toluenediamine, 2,6-toluenediamine, p-xylenediamine, m-xylenediamine, 1,4-cyclohexane bis(methylamine), 1,3-cyclohexanebis(methylamine) and the like; glycidyl ester compounds derived from aromatic carboxylic acids such as p-hydroxybenzoic acid, m-hydroxybenzoic acid, terephthalic acid, isophthalic acid and the like; hydantoin type epoxy compounds derived from 5,5-dimethylhydantoin and the like; alicyclic epoxy resins such as 2,2-bis(3,4-epoxycyclohexyl)propane, 2,2-bis[4-(2,3-epoxypropyl)cyclohexyl]propane, vinylcyclo-hexane dioxide, 3,4-epoxycyclohexymethyl-3,4-epoxy cyclohexanecarboxylate and the like; N,N-diglycidylaniline; and the like, and these epoxy resins may be used alone or in admixture of two or more. Among them, o-cresol-novolak type epoxy resins and glycidyl ether compounds of polyhydric phenols obtained by condensation of a phenol with an aromatic carbonyl compound are preferred in view of curability and heat resistance.

The epoxy curing agent may be a known one and includes active hydrogen-containing compounds capable of reacting with epoxy groups, for example, polyphenol compounds such as bisphenol A, tetrabromobisphenol A, bisphenol F, bisphenol S, bis(4-hydroxyphenyl)cyclohexane, bis(4-hydroxyphenyl)ethane, 1,3,3-trimethyl-1-m-hydroxyphenylindan-5 or 7-ol, 1,3,3-trimethyl-1-p-hydroxyphenylindan-6-ol, resorcin, hydroquinone, catechol; phenol-novolak resins obtained by reaction of formaldehyde with a phenol such as phenol, o-cresol or the like; polycarboxylic acids such as maleic acid, phthalic acid, nadic acid, methyltetrahydrophthalic acid, methylnadic acid and the like; anhydrides of these acids; polyamines such as diaminodiphenylmethane, diaminodiphenylsulfone, diaminodiphenyl ether, phenylenediamine, diaminodicyclohexylmethane, xylenediamine, toluenediamine, diaminodicyclohexane, dichlorodiaminodiphenylmethane (including their isomers), ethylenediamine, hexamethylenediamine and the like; dicyandiamide; tetramethylguanidine; and the like. Among them, phenol-novolak resins are preferred in view of curability and moisture resistance.

In the thermosetting resin composition of this invention, the amount of the curing accelerator used may be varied depending upon the curing rate required. The curing rate is varied depending upon the use. For example, in the case of sealing material, usually, 1–3 parts by weight of the curing accelerator is used per 100 parts by weight of the resin component.

In the thermosetting resin composition of this invention, the amount of each of the unsaturated imide compound, the curing accelerator and the epoxy resin used can be adequately varied depending upon the desired heat resistance and the like. However, generally, it is preferable to select the amounts so that the weight fraction of the unsaturated imide compound {unsaturated imide compound/[unsaturated imide compound+epoxy resin+epoxy curing agent]} becomes 0.9–0.1, more preferably 0.7–0.3. When the amount of the unsaturated imide compound blended goes beyond the above range, the moisture resistance and heat resistance are deteriorated.

Also, the amounts of the epoxy resin and the curing agent blended are preferably equal to each other, and when the amounts are quite different, moisture resistance and heat resistance are deteriorated.

The thermosetting resin composition of this invention may, if necessary, contain a filler. Examples of the filler are fused silica, crystalline silica, alumina, talc, calcium carbonate, titanium white, clay, asbestos, mica, red iron oxide, glass fiber and the like, and among them, molten silica, crystalline silica and alumina are particularly preferable.

The amount of the filler compounded can be varied depending upon the purpose, and when the composition is used in sealing a semiconductor, the amount of the filler is preferably 30–90%, more preferably 60–85%, by weight based on the total weight of the resin composition. When the amount is less than 30% by weight, the moisture resistance is inferior and when it exceeds 90% by weight, the formability is not satisfactory.

In this invention, if necessary, there may be added to the composition natural wax, synthetic wax, higher fatty acid and metal salt, a releasing agent such as paraffin or the like, a coloring agent such as carbon black, and a surface treating agent such as silanecoupling agent or the like. A flame retardant such as antimony trioxide, phosphorus compound, brominated epoxy resin or the like may be added to the composition. Brominated epoxy resin is particularly preferable for obtaining the flame retardant effect.

In order to make the stress of the composition low, various elastomers may be added to the composition or previously reacted with the composition. Specific examples of the elastomer are additive type and reactive type elastomers such as polybutadiene, butadiene-acrylonitrile copolymer, silicone rubber, silicone oil and the like.

The thermosetting resin composition thus obtained may be melt-mixed by means of a conventional mixer such as roll, Ko-kneader or the like to be formed into a compound.

The thermosetting resin composition of this invention is used suitably in sealing electronic parts such as semiconductor and the like. The sealing of electronic parts such as semiconductor or the like with the thermosetting resin composition of this invention may be effected by cure-molding the composition by a conventional molding method such as transfer molding, compression molding, injection molding or the like.

DESCRIPTION OF PREFERRED EMBODIMENTS

This invention is further explained in more detail below referring to Examples, which are merely by way of illustration and not by way of limitation.

EXAMPLE 1

(Synthesis of diamino compound)

(1) Synthesis of bisphenols

In a 1-liter, four-necked flask equipped with a thermometer, a stirrer and a dropping funnel were placed 188 g of phenol, 188 g of toluene and 13 g of a boron trifluoride-ether complex, and they were dissolved under a nitrogen stream. A solution of 136 g of dipentene in 136 g of toluene was dropwise added to the resulting solution in 2 hours at a temperature of 0°–5° C. Further, the reaction was continued at a temperature of 0°–5° C. for 2 hours, at room temperature for 2 hours and then the temperature was elevated to 60° C. to complete the reaction. To the reaction mixture was added 250 g of a 5% aqueous sodium hydroxide solution, and the resulting mixture was stirred at room temperature for 10 minutes, upon which the brown solution was changed to a pale yellow solution. After liquid separation, the organic layer was washed with 250 g of pure water three times. The reaction mixture was subjected to reflux under reduced pressure in a Dean-Stark azeotropic dehydration apparatus to remove water. The solution was concentrated under reduced pressure and the concentrate was allowed to stand to obtain crystals. The crystals were warmed under reduced pressure to dry them, thereby obtaining 176.9 g (yield: 61.0%) of a colorless, transparent compound. The hydroxyl group equivalent of this compound was 162 g/eq.

(2) Synthesis of dinitro compound

In a 1-liter, four-necked flask equipped with a thermometer, a stirrer and a dropping funnel were placed 77.5 g of the bisphenol, namely the reaction product of dipentene with phenol obtained in (1) above, 78.5 g of p-chloronitrobenzene and 263.2 g of 1-methyl-2-pyrrolidone, and they were dissolved at 50° C. under a nitrogen stream. Thereto was added 20.6 g of 99% sodium hydroxide powder, and the resulting mixture was kept at 50° C. for 0.5 hour, after which the temperature was elevated to 80° C. The reaction was continued at 80°–85° C. for 3 hours, and the disappearance of the starting polyphenol was confirmed by LC (high performance liquid chromatography, the same applies hereinafter). The temperature was elevated to 125° C., at which the reaction mixture was kept for 3 hours, and the inner pressure was gradually reduced to 200 Torr to recover the water formed by the reaction in the system. Subsequently, the inner pressure was carefully reduced to 125 Torr to recover 1-methyl-2-pyrrolidone which is the reaction solvent to the extent that the fluidity of the reaction mixture was not lost.

The reaction mixture was poured into 600 g of pure water with stirring, and the precipitates separated were collected by filtration and then washed with 300 g of water and then with 200 g of warmed methanol. The precipitates thus obtained were warmed under reduced pressure to be dried, thereby obtaining 133.5 g (yield: 97.7%) of the objective compound. This compound was bis(4-nitrophenoxyphenyl)menthane. The infrared absorption spectra of this compound indicated absorptions at 1340 $cm^{-1}$ and 1512 $cm^{-1}$ (nitro group).

(3) Synthesis of diamino compound

In a 3-liter, four-necked flask were placed 113.3 g of the dinitro compound obtained in (2) above, 11 g of active carbon, 0.65 g of ferric chloride hexahydrate and 566.5 g of 2-methoxyethanol, and they were dissolved under a nitrogen stream. At a temperature of 70°–80° C., 40.0 g of hydrazine monohydrate was added to the mixture dropwise in 3 hours, and the reaction was continued at the same temperature and the disappearance of the starting dinitro compound was confirmed by LC. The reaction was further continued for 3 hours, and thereafter, the reaction mixture was neutralized with a 10% aqueous sodium hydroxide solution, after which the active carbon was removed by hot-filtration. The solvent was 80% removed by distillation under reduced pressure, and then, the reaction mixture was dropped into 2 kg of water with stirring. The pH of the aqueous layer was adjusted to 7.0–9.5 with a 10% aqueous sodium hydroxide solution, and then the stirring was continued, after which the precipitates were collected by filtration. The precipitates were washed with water and dried by warming under reduced to obtain 100.8 g (yield: 99.5%) of the objective compound. This compound was bis(4-aminopheoxyphenyl)menthane. This indicated a solubility (the number of grams of solute in 100 g of solution, the same applied hereinafter) of 50 or more in general-purpose solvents such as acetone, toluene and the like. The physical properties of this compound were as follows:

Mass spectra $M^+$: 506 Amine equivalent (by titration method): 254 g/eq $^1$H-NMR spectra δ: 0.6–2.1 ppm (m, aliphatic), 2.7 ppm (m, methine), 3.5 ppm (brs, amino group), 6.6–7.3 ppm (m, aromatic)

Infrared absorption spectra: 1228 $cm^{-1}$ (ether bond), 3210, 3360, 3440 $cm^{-1}$ (amino bond)

Elementary analysis (as $C_{34}H_{38}N_2O_2$): Calcd.: C 80.60%, H 7.56%, N 5.53% Found: C 80.5%, H 7.7%, N 5.4

EXAMPLE 2

(Synthesis of diamino compound)

(1) Synthesis of bisphenol

The same procedure as in Example 1 (1) was repeated, except that 2,6-xylenol was substituted for the phenol and the reaction temperature was changed to 110° C. to obtain a toluene solution of the reaction mixture, and this solution was concentrated under reduced pressure to remove the toluene. Subsequently, nitrogen was introduced under reduced pressure, and then the unreacted matter was removed by steam distillation to obtain 209.4 g (yield: 55.1%) of pale brown solid. The hydroxyl group equivalent was 191 g/eq.

(2) Synthesis of dinitro compound

The same procedure as in Example 1 (2) was repeated, except that 91.3 g of the reaction product of dipentene and 2,6-xylenol obtained in (1) above was substituted for the bisphenol, to obtain 146.6 g (yield: 98.3%) of the objective compound. This compound was bis[4-(4-nitrophenoxy)-3,5-dimethylphenyl]menthane. The infrared absorption spectra of this compound indicated absorptions at 1338 $cm^{-1}$ and 1515 $cm^{-1}$ (nitro group).

(3) Synthesis of diamino compound

The same procedure as in Example 1 (3) was repeated, except that 120 g of the compound obtained in (2) above was substituted for the dinitro compound, to obtain 107.1 g (yield: 98.8%) of the objective compound. This compound was bis[4-(4-aminophenoxy)-3,5-dimethylphenyl]menthane. This compound indicated a solubility of 50 or more in general-purpose solvents such as acetone, toluene or the like. Other physical properties of this compound were as follows:

Mass spectra $M^+$: 562 Amine equivalent (by titration method): 282 g/eq $^1$H-NMR spectra δ: 0.5–2.4 ppm (m, aliphatic), 2.1 ppm (s, methyl), 2.7 ppm (m, methine), 3.4 ppm (brs, amino group ), 6.6–7.3 ppm (m, aromatic )

Infrared absorption spectra: 1218 $cm^{-1}$ (ether bond), 3210, 3350, 3430 $cm^{-1}$ (amino bond)

Elementary analysis (as $C_{38}H_{46}N_2O_2$): Calcd.: C 81.10%, H 8.23%, N 4.98% Found: C 81.0% H 8.5%, N 5.0[{]jf44a

EXAMPLE 3

(Synthesis of diamino compound)

(1) Synthesis of bisphenol

In a 1-liter, four-necked flask equipped with a thermometer, a stirrer and a dropping funnel were placed 488 g of 2,6-xylenol and 7.1 g of a boron trifluoride-ether complex, and the resulting mixture was warmed under a nitrogen stream to dissolve the mixture. The inner temperature was kept at 100°–110° C. and 132.2 g of dicyclopentadiene was dropped into the solution at a temperature of 100°–110° C. in 4 hours. The reaction was continued for a further 6 hours at a temperature of 110° C., and thereafter, the contents of the flask were transferred to a separate vessel. To the contents were added 1,200 g of toluene and 1,000 g of a 10% aqueous sodium bicarbonate solution, and the resulting mixture was stirred at room temperature for 10 minutes, upon which the brown solution was changed to a pale yellow solution. After liquid separation, the organic layer was washed with 500 g of pure water three times. The reaction mixture was heated under reflux in a Dean-Stark azeotropic dehydration apparatus to remove water. The solution was concentrated under reduced pressure and the excessive 2,6-xylenol was then removed by distillation. Subsequently, nitrogen was introduced under reduced pressure, and thereafter, the unreacted matter was removed by steam distillation to obtain 328.3 g (yield: 87.2%) of a pale yellow solid of the objective compound. The hydroxyl group equivalent of this compound was 188 g/eq.

(2) Synthesis of dinitro compound

The same procedure as in Example 1 (2) was repeated, except that 300 g of the reaction product of dicyclopentadiene and 2,6-xylenol obtained in (1) above was substituted for the bisphenol, to obtain 482.3 g (yield: 97.7%) of the objective compound. This compound was bis[4-(4-nitrophenoxy)-3,5-dimethylphenyl]dicyclopentane. The infrared absorption spectra of this compound indicated absorptions at 1338 and 1510 $cm^{-1}$ (nitro group).

(3) Synthesis of diamino compound

The same procedure as in Example 1 (3) was repeated, except that 309.4 g of the compound obtained in (2) above was substituted for the dinitro compound, to obtain 277.2 g (yield: 99.2%) of the objective compound. This compound was bis[4-(4-aminophenoxy)-3,5 -dimethylphenyl]dicyclopentane. This indicated a solubility of 50 or more in general-purpose solvents such as acetone, toluene and the like. Other physical properties of this compound were as follows:

Mass spectra $M^+$: 558 Amine equivalent (by titration method): 280 g/eq $^1$H-NMR spectra δ: 1.1–3.5 ppm (m, aliphatic), 2.1 ppm (s, methyl), 3.2 ppm (brs, amino group), 6.6–7.1 ppm (m, aromatic)

Infrared absorption spectra: 1206 $cm^{-1}$ (ether bond) 3200, 3350, 3430 $cm^{-1}$ (amino bond)

Elementary analysis (as $C_{38}H_{42}N_2O_2$): Calcd.: C 81.69%, H 7.57%, N: 5.01% Found: C 81.5%, H 7.7%, N: 4.9

EXAMPLE 4

(1) Synthesis of dinitro compound

The same procedure as in Example 1 (2) was repeated, except that a reaction product of 2,6-xylenol and dicyclopentadiene (oligomer) (DXP-L-9-1,a trade name of Japan Petroleum Co., Ltd., hydroxyl group equivalent: 191 g/eq) was substituted for the bisphenol, to obtain an oligomer of 2,6-xylenol and dicyclopentadiene having a 4-(4-nitrophenoxy)-3,5-dimethylphenyl group.

(2) Synthesis of diamino compound

The same procedure as in Example 1 (3) was repeated, except that the compound obtained in (1) above was substituted for the dinitro compound, to obtain an oligomer of 2,6-xylenol and dicyclopentadiene having terminal 4-(4-aminophenoxy)-3,5-dimethylphenyl groups. The measurement by GPC indicated that the oligomer contained 90% of [4-(4-aminophenoxy)-3,5-dimethylphenyl]dicyclopentane. This oligomer had an amine equivalent of 275 g/eq.

EXAMPLE 5

[Synthesis of N,N'-bis(4-aminophenoxyphenyl)menthane bismaleimide (Compound 1)]

In a 300-ml, four-necked flask were placed 10.8 g of maleic anhydride and 25.2 g of acetone, and they were dissolved with stirring under a nitrogen stream. While the temperature was kept at room temperature- 35° C. a solution in 59.1 g of acetone of 25.3 g (amine equivalent: 253 g/eq) of the bis(4-aminophenoxyphenyl)menthane obtained in Example 1 was dropped into the solution in 2 hours, and the stirring was further continued for 3 hours. Subsequently, 3.04 g of triethylamine was added, and the resulting mixture was stirred at room temperature for 0.5 hour, after which 0.11 g of nickel acetate was added thereto and the temperature was elevated to 40° C. Thereinto was dropped 13.3 g of acetic anhydride in 1 hour, and thereafter, the reaction was continued at the same temperature. After completion of the reaction, 200 g of pure water was dropped thereinto, upon which the reaction mixture was precipitated. The precipitates were collected by filtration, washed with water, then with methanol to dry the crystals. The crystals were recrystallized from methyl Cellosolve/isopropanol to obtain 23.5 g (yield: 70.6%) of yellow precipitates. The solubilities of the precipitates in acetone and toluene are shown in Table 1. Other physical properties were as follows:

Mass spectra $M^+$: 666 Melting point: 96°–98° C.

$^1$H-NMR spectra δ: 0.6–2.1 ppm (m, aliphatic), 2.8 ppm (m, methine), 6.8 ppm (s, imido group), 6.9–7.4 ppm (m, aromatic)

Infrared absorption spectra: 1.238 $cm^{-1}$ (ether bond), 1712 $cm^{-1}$ (imido bond)

Elementary analysis (as $C_{42}H_{38}N_2O_6$): Calcd.: C 75.66%, H 5.74%, N 4.20% Found: C 75.5%, H 5.8%, N 4.1%

EXAMPLE 6

[Synthesis of N,N'-bis[4-(4-aminophenoxy)-3,5-dimethylphenyl]menthane bismaleimide (Compound 2)]

In a 500-ml, four-necked flask were placed 32.6 g of maleic anhydride and 76 g of acetone, and they were dissolved with stirring under a nitrogen stream. While the temperature was kept at room temperature-35° C., a solution in 198 g of acetone of 84.9 g of the bis[4-(4-aminophenoxy)-3,5-dimethylphenyl]menthane (amine equivalent: 281 g/eq) obtained in Example 2 was dropped in 2 hours. The stirring was continued for a further 3 hours. Subsequently, 3.04 g of triethylamine was added, and the resulting mixture was stirred at room temperature for 0.5 hour, after which 0.29 g of nickel acetate was added thereto and the temperature was elevated to 40° C. Thereinto was dropped 40.1 g of acetic anhydride in 1 hour, and then kept at the same temperature until the reaction was completed. After completion of the reaction, the reaction mixture was poured into 600 g of pure water. The resulting precipitates were collected by filtration, washed with water, then with methanol, and warmed under reduced pressure to be dried. Yellow precipitates were obtained in an amount of 108.0 g (yield: 98.9%). A part thereof was recrystallized from methyl Cellosolve/isopropanol. The solubilities thereof in acetone and toluene are shown in Table 1. Other physical properties were as follows:

Mass spectra $M^+$: 722

$^1$H-NMR spectra δ: 0.6–2.2 ppm (m, aliphatic), 2.1 ppm (m, methyl group), 6.8 ppm (s, imido group), 6.8–7.2 ppm (m, aromatic)

Infrared absorption spectra: 1222 $cm^{-1}$ (ether bond), 1716 $cm^{-1}$ (imido bond)

Elementary analysis (as $C_{46}H_{46}N_2O_6$): Calcd.: C 76.43%, H 6.41%, N 3.88% Found: C 76.2%, H 6.6%, N 3.9%

EXAMPLE 7

[Synthesis of N,N'-bis[4-(4-aminophenoxy)-3,5-dimethylphenyl]dicyclopentane bismaleimide (Compound 3)]

In a 1-liter, four-necked flask were placed 51.3 g of maleic anhydride and 119.7 g of acetone, and they were dissolved with stirring under a nitrogen stream. While the temperature was kept at room temperature- 35° C., a solution in 309.2 g of acetone of 132.5 g (amine equivalent: 279 g/eq) of the bis[4-(4-aminophenoxy)- 3,5-dimethylphenyl]dicyclopentane obtained in Example 3 was dropped in 2 hours. The resulting mixture was stirred for a further 3 hours. Subsequently, 14.4 g of triethylamine was added and the resulting mixture was stirred at room temperature for 0.5 hour, after which 0.50 g of nickel acetate was added and the temperature was elevated to 40° C. Acetic anhydride (63.0 g) was dropped in 1 hour, and thereafter, the resulting mixture was kept at the same temperature until the reaction was completed. After completion of the reaction, the reaction mixture was poured into 1,000 g of pure water. The resulting crystals were collected by filtration, washed with water, then with methanol, and warmed under reduced pressure to be dried. Yellow precipitates of the objective compound were obtained in an amount of 141.7 g (yield: 83.0%). The solubilities thereof in acetone and toluene are shown in Table 1. Other physical properties were as follows:

Mass spectra $M^+$: 718

$^1$H-NMR spectra δ: 1.0–2.4 ppm (m, aliphatic), 2.1 ppm (m, methyl group), 2.7 ppm (m, methine), 6.8 ppm (s, imido group), 6.6–7.3 ppm (m, aromatic)

Infrared absorption spectra: 1222 $cm^{-1}$ (ether bond), 1714 $cm^{-1}$ (imido bond)

Elementary analysis (as $C_{46}H_{42}N_2O_6$): Calcd.: C 76.86%, H 5.89%, N 3.90% Found: C 76.8%, H 6.0%, N 3.9%

EXAMPLE 8

[Synthesis of maleimide derived from oligomer of 2,6-xylenol and dicyclopentadiene having [4-(4-aminophenoxy)-3,5-dimethylphenyl group]

In a 1-liter, four-necked flask were placed 58.8 g of maleic anhydride and 137.2 g of acetone, and they were dissolved with stirring under a nitrogen stream. While the temperature was kept at room temperature- 35° C., a solution in 350 g of acetone of 150.0 g of the oligomer of 2,6-xylenol and dicyclopentadiene having a 4-(4-aminophenoxy)-3,5-dimethylphenyl group obtained in Example 4 was dropped in 2 hours. The stirring was continued for a further 3 hours. Subsequently, 16.6 g of triethylamine was added, and the resulting mixture was stirred at room temperature for 0.5 hour. Thereafter, 0.58 g of nickel acetate was added and the temperature was elevated to 40° C., after which 72.4 g of acetic anhydride was dropped in 1 hour and the resulting mixture was kept at the same temperature until the reaction was completed. After completion of the reaction, the reaction mixture was poured into 1,000 g of pure water, and the resulting precipitates were collected by filtration, washed with water, then with methanol and warmed under reduced pressure to be dried. Yellow precipitates of the objective-compound were obtained in an amount of 189.4 g (yield: 97.9%). The solubilities thereof in acetone and toluene are shown in Table 1, and other physical properties were as follows:

Mass spectra $M^+$: 718

$^1$H-NMR spectra δ: 1.0–2.5 ppm (m, aliphatic ), 2.7 ppm (m, methine ), 6.8 ppm ( s, imido group ), 6.5–7.3 ppm ( m, aroma tic )

Infrared absorption spectra: 1220 $cm^{-1}$ (ether bond ), 1714 $cm^{-1}$ ( imido bond )

TABLE 1

|  | Acetone | Toluene |
|---|---|---|
| Compound 1[1) | O | O |
| Compound 2[2) | O | O |
| Compound 3[3) | O | O |
| Compound 4[4) | O | O |
| Comparative compound[5) | X | X |

Note:
O: solubility of 40 or more as measured at 25° C.
X: solubility of less than 40 as measured at 25° C.
[1)N,N'-bis(4-aminophenoxyphenyl)menthane bismaleimide (product of Example 5)
[2)N,N'-bis[4-(4-aminophenoxy)-3,5-dimethyl-phenyl]menthane bismaleimide (product of Example 6)
[3)N,N'-bis[4-(4-aminophenoxy)-3,5-dimethyl-phenyl]dicyclopentane bismaleimide (product of Example 7)
[4)Maleimide derived from oligomer of 2,6-xylenol and dicyclopentadiene having a 4-(4-aminophenoxy)-3,5-dimethylphenyl group (product of Example 8)
[5)N,N'-4,4'-diphenylmethane bismaleimide (Bestlex BH-180, a trade name of Sumitomo Chemical Co., Ltd.)

Application Examples 1 to 3 and Comparative Application Example 1

Each of Compounds 1, 2 and 3 obtained as unsaturated imide compounds in Examples 5, 6 and 7, respectively, was compounded with 4,4'-diaminodiphenylmethane (Sumicure M, a trade name of Sumitomo Chemical Co., Ltd.) as a curing agent, and the resulting compound was press-formed at 200° C. at 70 kg/cm$^2$ for 1 hour, and then cured at 200° C. for 4 hours to obtain cured products having a thickness of 2 mm.

The same procedure as above was repeated, except that N,N'-4,4'-diphenylmethane bismaleimide (Bestlex BH-180, a trade name of Sumitomo Chemical Co., Ltd.) was used as the unsaturated imide compound to prepare a cured product (Comparative Application Example 1).

The physical properties of these cured products are shown in Table 2.

Incidentally, the methods of measuring physical properties of the cured products were as follows:

Heat resistance: Indicated by glass transition temperature (Tg). Measured by means of a thermomechanical analysis apparatus (SHIMADZU DT-4).

Flexural strength, flexural modulus: Measured according to JIS K-6911 by means of an Instron type universal material tester (SHIMADZU IS-10T) at 240° C.

Water absorption: Indicated by absorption afterhaving been immersed with boiling for 3 hours.

TABLE 2

|  | Application Example 1 | Application Example 2 | Application Example 3 | Comparative Application Example 1 |
|---|---|---|---|---|
| Compounding recipe |  |  |  |  |
| Compound 1*[1) (g) | 89.4 | — | — | — |
| Compound 2*[2) (g) | — | 90.1 | — | — |
| Compound 3*[3) (g) | — | — | 90.1 | — |
| BH-180*[4) (g) | — | — | — | 81.8 |
| DDM*[5) (g) | 10.6 | 9.9 | 9.9 | 18.2 |
| Physical properties |  |  |  |  |
| Heat resistance (° C.) | 205 | 220 | 232 | 223 |
| Flexural strength (kg/mm$^2$) | 13.2 | 14.9 | 15.0 | 14.3 |
| Flexural modulus (kg/mm$^2$) | 349 | 381 | 403 | 424 |
| Water absorption | 1.55 | 1.61 | 1.59 | 2.91 |

Note:
[1)N,N'-bis(4-aminophenoxyphenyl)menthane bismaleimide
[2)N,N'-bis[4-(4-aminophenoxy)-3,5-dimethylphenyl]menthane bismaleimide
[3)N,N'-bis[4-(4-aminophenoxy)-3,5-dimethylphenyl]dicyclopentane bismaleimide
[4)N,N'-4,4'-diphenylmethane bismaleimide (Bestlex BH-180, a trade name of Sumitomo Chemical Co., Ltd.)
[5)4,4'-Diaminodiphenylmethane (Sumicure M, a trade name of Sumitomo Chemical Co., Ltd.)

EXAMPLE 9

[Synthesis of bis(4-nitrophenoxyphenyl) menthane (dinitro compound)]

In a 5-liter, four-necked flask equipped with a thermometer, a stirrer and a dropping funnel were placed 746.3 g of YP-90 (a trade name of Yasuhara Chemical for reaction product of dipentene and phenol having a hydroxyl group equivalent of 162 g/eq), 724.8 g of p-chloronitrobenzene and 2.457 g of dimethylacetamide (referred to hereinafter as DMAc), and they were dissolved at 50° C. under a nitrogen stream, after which 642.2 g of anhydrous potassium carbonate was added. The resulting mixture was heated to 140° C. and reaction was continued at 140°–145° C. for 15 hours. The inner temperature was lowered to 100° C., and thereafter, the resulting salt was removed by filtration. This salt was washed with 200 g of dimethylacetamide and the washing was combined with the filtrate to obtain a DMAc solution of bis(4-nitrophenoxyphenyl)menthane. A part of this solution was concentrated under reduced pressure and washed with water, then with methanol under reflux for 1 hour, after which pale yellow precipitates were collected by filtration, and then dried under reduced pressure. The purity thereof as measured by LC was 97.80%, and absorptions due to nitro group at 1340 cm$^{-1}$ and 1512 cm$^{-1}$ were observed in the infrared absorption spectra.

EXAMPLE 10

[Synthesis of bis(4-aminophenoxyphenyl)menthane (diamino compound)]

In a 500-ml autoclave were placed 350 g of the DMAc solution (the concentration was adjusted to 33.3% by weight) of (4-nitrophenoxyphenyl)methane obtained in Example 9 and 4.6 g of 5% palladium/active carbon catalyst. The inner pressure of the autoclave was reduced, and then returned to the original pressure with nitrogen to remove the oxygen in the system. Subsequently, the pressure was reduced again, and then returned to the original with hydrogen, and this operation was repeated three times to substitute the inner gas of the autoclave with hydrogen. Under a hydrogen atmosphere, the inner temperature was elevated to 80°±5° C. and the reaction was continued at the same temperature for 4 hours. The inner pressure was elevated to 1.5 atms and the reaction was continued for a further 30 minutes to complete the reduction reaction.

The pressure of the autoclave was reduced and then returned to the original pressure with nitrogen to remove the hydrogen in the autoclave. The reaction mixture was filtered through a Radiolite (a trade name of Mizusawa Kagaku for a kind of filter aid)-coated filter paper in a separate filtering apparatus at 80° C. and the filtrate was washed with 20 g of DMAc, and then, placed in a 1-liter flask, after which chlorobenzene was added thereto. The resulting mixture was subjected to azeotropic dehydration under reduced pressure and then the water in the system was removed by means of a Dean-Stark azeotropic dehydration apparatus. Subsequently, the chlorobenzene was recovered under reduced pressure to obtain a DMAc solution of (4-aminophenoxyphenyl)menthane. The purity of the diamino compound in the solution was found to be 98.2% by LC.

A part of the solution was concentrated under reduced pressure and then dissolved again in toluene. The resulting solution was washed with a 20% by weight aqueous sodium chloride solution and then dried over magnesium sulfate. After the drying, the drying agent was removed by filtration, and the filtrate was subjected to distillation under reduced pressure to obtain a standard product. This was pale brown and glass-like. Physical properties of this product were as follows:

Mass spectra M$^+$: 506 Amine equivalent (by titration method): 254 g/eq $^1$H-NMR spectra δ: 0.6–2.1 ppm (m, aliphatic), 2.7 ppm (m, methine), 3.5 ppm (brs, amino group), 6.6–7.3 ppm (m, aromatic)

Infrared absorption spectra: 1228 cm$^{-1}$ (ether bond), 3210, 3360, 3440 cm$^{-1}$ (amino bond)

EXAMPLE 11

[Synthesis of bis (4-aminophenoxyphenyl)menthane (diamino compound)]

In a 500-ml autoclave were placed 50 g of DMAc and 4.0 g of 5% palladium/alumina catalyst. The pressure of the autoclave was reduced and then returned to the original pressure with nitrogen to remove the oxygen in the system. Subsequently, the pressure of the autoclave was again reduced and then returned to the original pressure with hydrogen, and this operation was repeated three times to substitute the gas in the autoclave with hydrogen. Under a hydrogen atmosphere, the inner temperature of the autoclave was elevated to 80°±5° C. and 300 g of the DMAc solution (concentration was adjusted to 33.3% by weight) of bis(4-nitrophenoxyphenyl)menthane obtained in Example 9 was dropped into the autoclave at 1 atm through a dropping means in 2 hours, and at the same temperature, the reaction was continued for 2 hours to complete the reduction reaction.

The pressure of the autoclave was reduced and then returned to the original pressure with nitrogen to remove the hydrogen in the system. The reaction mixture was filtered at 80° C. to remove the catalyst, and the filtrate was washed with 20 g of DMAc to obtain a DMAc solution of bis(4-aminophenoxyphenyl)menthane. The purity of the diamino compound in the solution was found to be 98.9% by LC.

The retention time of this diamino compound found by the LC anyalsis was completely identical with that obtained in Example 10.

EXAMPLE 12

[Synthesis of N,N'-bis(4-aminophneoxyphenyl)menthane bismaleimide (unsaturated imide compound)]

In a 5-liter, four-necked flask were placed 237.3 g of maleic anhydride and 2,373 g of chlorobenzene, and they were dissolved with stirring under a nitrogen stream. Into the flask was dropped 1,625.1 g of the DMAc solution (concentration was adjusted to 34.3% by weight) of bis(4-aminophenoxyphenyl)menthane obtained in Example 10 through a dropping funnel at 25°±5° C. in 2 hours. The reaction was continued at 35° C. for 2 hours to complete the formation of amic acid.

Subsequently, 10.46 g of p-toluenesulfonic acid monohydrate was added, and the resulting mixture was subjected to dehydration-ring-closure reaction at atmospheric pressure at a temperature of 130° to 140° C. The reaction was allowed to proceed while the water formed was taken out of the system by means of a Dean-Stark azeotropic dehydration apparatus. The reaction was completed in 5 hours.

Subsequently, chlorobenzene and then DMAc were recovered under reduced pressure in a total amount of 93%. The crude product obtained in this case was resinous. To the product was added 674 g of propylene glycol monomethyl ether and the resulting mixture was heated to 60° C. and the resulting solution was cooled and then poured into 1,685 g of 2-propanol, after which the resulting precipitates were collected by filtration. The precipitates were washed with 2-propanol and then with methanol, and dried under reduced pressure to obtain 669 g (yield: 91.2 %) of pale yellow precipitates. From GPC, it was found that 85% of N,N'-bis(4-aminophenoxyphenyl)menthane bismaleimide and 15% of the oligomer component of the bismaleimide were contained. The oligomer component acts effectively as a thermosetting resin, and therefore, it is usually not necessary to separate the same (in the following Examples, the same applies). The infrared absorption spectra of the product indicated an absorption due to ether bond at 1238 cm$^{-1}$ and an absorption due to imido bond at 1712 cm$^{-1}$.

EXAMPLE 13

[Synthesis of
N,N'-bis(4-aminophenoxyphenyl)menthane
bismaleimide (unsaturated imide compound)]

The same procedure as in Example 12 was repeated, except that 95.0 g of a cationic ion-exchange resin (Amberlist 15, a trade name of Organo Co., Ltd.) was substituted for the p-toluenesulfonic acid monohydrate catalyst, and the dehydration-ring-closure reaction was effected at a temperature of 130° to 140° C. for 5 hours. The catalyst was removed by filtration, and the filtrate was subjected to the same after-treatment as in Example 12 to obtain 645 g (yield: 88.0% ) of pale yellow precipitates. From GPC, it was found that 82% of N,N'-bis ( 4-aminophenoxyphenyl)menthane bismaleimide and 18% of the oligomer component of the bismaleimide were contained.

EXAMPLE 14

[Synthesis of
N,N'-bis(4,aminophenoxyphenyl)menthane
bismaleimide (unsaturated imide compound)]

In a 5-liter, four-necked flask were placed 237.3 g of maleic anhydride and 2,373 g of chlorobenzene, and they were dissolved with stirring under a nitrogen stream. A solution in 1,067.8 g of DMAc of 557.3 g of bis(4-aminophenoxyphenyl)menthane was dropped into the flask through a dropping funnel at 25°±5° C. in 2 hours. Reaction was continued at 35° C. for 2 hours to complete the formation of amic acid.

Subsequently, 10.46 g of p-toluenesulfonic acid monohydrate was added, and the resulting mixture was subjected to dehydration-ring-closure reaction under reduced pressure at 100° C. for 1 hour and at 110° C. for 1 hour. The reaction was allowed to proceed while the water formed was taken out of the system by use of a Dean-Stark azeotropic dehydration apparatus (the first stage preliminary reaction). Subsequently, the pressure was returned to the atmospheric pressure while the azeotropic dehydration was continued and then the temperature was adjusted to 135° C. The reaction was completed at 135° C. in 3 hours (the main reaction in the second stage).

Subsequently, under reduced pressure, chlorobenzene and then DMAc were recovered in a total amount of 91%. The crude product obtained in this case was resinous. To the product was added 674 g of propylene glycol monomethyl ether and the resulting mixture was heated to 60° C., after which the solution thus obtained was cooled and then poured into 1,685 g of 2-propanol. The precipitates thus formed were collected by filtration, and washed with 2-propanol and then with methanol, and thereafter dried under reduced pressure to obtain 698 g (yield: 95.2%) of pale yellow precipitates. From GPC, it was found that 96% of N,N'-bis(4-aminophenoxyphenyl)menthane bismaleimide and 4% of the oligomer component of the bismaleimide were contained. Physical properties thereof were as follows:

Mass spectra M+: 666 Melting point: 96°–98° C.

$^1$H-NMR spectra δ: 0.6–2.1 ppm (m, aliphatic), 2.8 ppm (m, methine), 6.8 ppm (s, imido group), 6.9–7.4 ppm (m, aromatic)

Infrared absorption spectra: 1238 cm$^{-1}$ (ether bond), 1712 cm$^{-1}$ (imido bond)

Comparative Example 1

The same procedure as in Example 14 was repeated, except that the azeotropic dehydration under reduced pressure (the first stage preliminary reaction) was not effected and only the main reaction was effected. The purity (GPC) of the product obtained and the time required for the reaction are shown in Table 3.

Comparative Example 2

The same procedure as in Example 14 was repeated, except that toluene was substituted for the chlorobenzene and only azeotropic dehydration was carried out at atmospheric pressure at a temperature of 110°–120° C. The purity (GPC) of the product obtained and the time required for the reaction are shown in Table 3.

TABLE 3

|  | Product purity (GPC) | Reaction time (azeotropic dehydration) |
| --- | --- | --- |
| Example 14 | 96% | 4.5 hours |
| Comp. Example 1 | 94% | 12 hours |
| Comp. Example 2 | 82% | 3.5 hours |

EXAMPLE 15

[Synthesis of
N,N'-bis(4-aminophenoxyphenyl)menthane
bismaleimide (unsaturated imide compound)]

The same procedure as in Example 14 was repeated, except that 95.0 g of a cationic ion-exchange resin [Amberlist 15 (a trade name of Organo Co., Ltd.)] was substituted for the p-toluenesulfonic acid monohydrate catalyst. The catalyst was separated by filtration, and the same after-treatment as in Example 14 was carried out to obtain 587 g (yield: 94.1%) of pale yellow precipitates. From GPC, it was found that 98% of N,N'-bis(4-aminophenoxyphenyl)menthane bismaleimide and 2% of the oligomer component of the bismaleimide were contained. The retention time thereof in LC was completely identical with that of the standard product in Example 14.

EXAMPLE 16

[Synthesis of
N,N'-bis(4-aminophenoxyphenyl)menthane
bismaleimide (unsaturated imide compound)]

In a 5-liter, four-necked flask were placed 237.3 g of maleic anhydride and 2,373 g of chlorobenzene, and they were dissolved with stirring under a nitrogen stream. Into the flask was dropped 1,625.1 g of a DMAc solution of bis(4-aminophenoxyphenyl)menthane through a dropping funnel at 25°±5° C. in 2 hours. Reaction was continued at 35° C. for 2 hours to complete the formation of amic acid.

Subsequently, 10.46 g of p-toluenesulfonic acid monohydrate was added thereto, and the resulting mixture was subjected to dehydration-ring-closure reaction at 100° C. for 1 hour and 110° C. for 1 hour under reduced pressure while the azeotropic dehydration was conducted, and subsequently, at 135° C. for 4 hours while the pressure was returned slowly to the atmospheric pressure. The reaction was allowed to proceed while the water formed was taken out of the system by use of a Dean-Stark azeotropic dehydration apparatus.

Subsequently, chlorobenzene and then DMAc were recovered in a total amount of 89% under reduced pressure. Subsequently, 2,200 g of methyl isobutyl ketone was added to prepare a solution. The solution was cooled to 60° C. and then neutralized by adding 1,000 g of water and sodium bicarbonate in such an amount that the pH of the aqueous layer became 5–7, and then subjected to washing and liquid separation. Further, the solution was washed with 1,000 g of a 15% aqueous sodium chloride solution two times at 60° C. and then subjected to liquid separation, and thereafter to remove the water by azeotropic dehydration under reduced pressure. The salt was removed by filtration. The filtrate was finally concentrated under reduced pressure, and when the conditions reached 150° C./5 Torr, the product was taken out in the molten state of the flask, to obtain pale brown solid in an amount of 724 g (yield: 98.7%). From GPC, it was found that 95% of N,N'-bis(4-aminophenoxyphenyl)menthane bismaleimide and 5% of high molecular weight component were contained. Physical properties thereof were as follows:

Mass spectra $M^+$: 666 Melting point: 96°–98° C.

$^1$H-NMR spectra δ: 0.6–2.1 ppm (m, aliphatic), 2.8 ppm (m, methine), 6.8 ppm (s, imido group), 6.9–7.4 ppm (m, aromatic)

Infrared absorption spectra: 1238 $cm^{-1}$ (ether bond), 1712 $cm^{-1}$ (imido bond)

EXAMPLEs 17 to 26

Compounds 1 to 4 obtained in Examples 5 to 8 were used as unsaturated imide compounds; glycidyl ether of o-cresol novolak [Sumiepoxy ESCN-195 (a trade name of Sumitomo Chemical Co., Ltd.)., epoxy equivalent: 201 g/eq, hydrolyzable chlorine content: 330 ppm] and glycidyl ether of polyphenol obtained by condensation of a phenol and hydroxybenzaldehyde (epoxy equivalent: 213 g/eq, hydrolyzable chlorine content: 200 ppm) (referred to hereinafter as PHB) were used as epoxy resins; phenol novolak (Tamanol 759, a trade name of Arakawa Kagaku K. K., OH equivalent: 106 g/eq) was used as a curing agent; triphenylphosphine and triethylammonium tetraphenylborate were used as curing accelerators; crushed fused silica (FS-891, a trade name of Denki Kagaku Kogyo K. K.) and spherical fused silica (FS-74, a trade name of Denki Kagaku Kogyo K. K.) were used as fillers; carnauba wax was used as a releasing agent; and SH-6040 (a trade name for coupling agent of Torey Dow Corning Silicone) and KBS-573, a trade name of Shin-etsu Kagaku Kogyo K. K.) were used as coupling agents. These were compounded in the amounts (g) shown in Tables 4 and 5, hot-kneaded on roll and transfer molded.

The molded products were further post-cured at 200° C. for 5 hours to obtain cured products. The compounding recipes, physical properties of thermosetting resin compositions and physical properties of cured products are shown in Tables 4 and 5.

Comparative Examples 3 and 4

The same procedure as in Example 17 was repeated, except that N,N'-(4,4'-diaminodiphenylmethane) bismaleimide (Bestlex BH-180, a trade name of Sumitomo Chemical Co., Ltd.) was used as the unsaturated imide compound, Sumiepoxy ESCN-195XL was used as the epoxy resin and Tamanol 759 was used as the epoxy curing agent (Comparative Example 3) or the same procedure as in Example 17 was repeated, except that Sumiepoxy ESCN-195 XL was used as the epoxy resin and Tamanol 759 was used as the epoxy curing agent (Comparative Example 4), to prepare cured products. The post-curing was effected at 200° C. for 5 hours (Comparative Example 3) or at 180° C. for 5 hours (Comparative Example 4). The compounding recipes, physical properties of thermosetting resin compositions and physical properties of cured products are shown in Table 5.

TABLE 4

| | | Example 17 | Example 18 | Example 19 | Example 20 | Comp. Ex. 21 | Comp. Ex. 22 |
|---|---|---|---|---|---|---|---|
| Compound 1 | | 50 | 60 | — | — | — | — |
| Compound 2 | | — | — | 50 | 60 | 60 | — |
| Compound 3 | | — | — | — | — | — | 50 |
| Compound 4 | | — | — | — | — | — | — |
| N,N-diphenylmethane bismaleimide | | — | — | — | — | — | — |
| ESCN-195XL | | 32.5 | — | 32.5 | 26.0 | — | 32.5 |
| PHG | | — | 26.7 | — | — | 26.7 | — |
| Phenol novolak | | 17.5 | 13.3 | 17.5 | 14.0 | 13.3 | 17.5 |
| Triphenyl phosphine | | 0.4 | ← | ← | ← | ← | ← |
| Triethylammonium tetraphenylborate | | 1.2 | ← | ← | ← | ← | ← |
| Crushed fused silica | | 63.3 | ← | ← | ← | ← | ← |
| Spherical fused silica | | 253.3 | ← | ← | ← | ← | ← |
| Carnauba wax | | 0.7 | ← | ← | ← | ← | ← |
| SH-6040 | | 1.0 | ← | ← | ← | ← | ← |
| KBM-573 | | 1.0 | ← | ← | ← | ← | ← |
| Gel time | sec | 41 | 40 | 38 | 41 | 38 | 37 |
| Spiral flow | inch | 35 | 37 | 42 | 44 | 40 | 35 |
| Barcol hardness | 935 | 72 | 72 | 76 | 75 | 75 | 84 |
| Glass transition temp. | °C. | 205 | 215 | 190 | 194 | 210 | 219 |
| Flexure at 20° C. | | | | | | | |
| Strength | kg/mm$^2$ | 17.5 | 15.4 | 13.0 | 12.6 | 13.3 | 15.5 |
| Modulus | kg/mm$^2$ | 1540 | 1440 | 1540 | 1550 | 1480 | 1610 |
| Flexure at 240° C. | | | | | | | |

TABLE 4-continued

|  |  | Example 17 | Example 18 | Example 19 | Example 20 | Comp. Ex. 21 | Comp. Ex. 22 |
|---|---|---|---|---|---|---|---|
| Strength | kg/mm² | 2.7 | 2.9 | 2.3 | 2.5 | 3.2 | 3.0 |
| Modulus | kg/mm² | 290 | 330 | 160 | 160 | 250 | 470 |
| Adhesion (Aluminum peel) | g/cm | 550 | 490 | 510 | 520 | 480 | 410 |
| Moisture absorption (72 hr) | % | 0.375 | 0.831 | 0.364 | 0.380 | 0.398 | 0.360 |
| Solder crack resistance | Cracked samples | 2 | 1 | 3 | 2 | 1 | 2 |

Note: "←" means the same as left.

TABLE 5

|  |  | Example 23 | Example 24 | Example 25 | Example 26 | Comp. Ex. 3 | Comp. Ex. 4 |
|---|---|---|---|---|---|---|---|
| Compound 1 |  | — | — | — | — | — | — |
| Compound 2 |  | — | — | — | — | — | — |
| Compound 3 |  | 60 | 60 | — | — | — | — |
| Compound 4 |  | — | — | 60 | 60 | — | — |
| N,N-diphenylmethane bismaleimide |  | — | — | — | — | 60 | — |
| ESCN-195XL |  | 26.0 | — | 26.0 | — | 26.0 | 64.9 |
| PHG |  | — | 26.7 | — | 26.7 | — | — |
| Phenol novolak |  | 14.0 | 13.3 | 14.0 | 13.3 | 14.0 | 35.1 |
| Triphenyl phosphine |  | 0.4 | ← | ← | ← | ← | 0.97 |
| Triethylammonium tetraphenylborate |  | 1.2 | ← | ← | ← | ← | — |
| Crushed fused silica |  | 63.3 | ← | ← | ← | ← | ← |
| Spherical fused silica |  | 253.3 | ← | ← | ← | ← | ← |
| Carnauba wax |  | 0.7 | ← | ← | ← | ← | ← |
| SH-6040 |  | 1.0 | ← | ← | ← | ← | 1.3 |
| KBM-573 |  | 1.0 | ← | ← | ← | ← | — |
| Gel time | sec | 35 | 36 | 35 | 37 | 32 | 35 |
| Spiral flow | inch | 31 | 37 | 30 | 31 | 28 | 45 |
| Barcol hardness | 935 | 84 | 82 | 84 | 82 | 75 | 75 |
| Glass transition temp. | °C. | 222 | 228 | 230 | 235 | 255 | 165 |
| Flexure at 20° C. |  |  |  |  |  |  |  |
| Strength | kg/mm² | 15.8 | 13.4 | 15.1 | 15.4 | 15.3 | 15.6 |
| Modulus | kg/cm² | 1600 | 1500 | 1670 | 1530 | 1740 | 1660 |
| Flexure at 240° C. |  |  |  |  |  |  |  |
| Strength | kg/mm² | 3.1 | 3.6 | 3.7 | 3.7 | 4.5 | 1.1 |
| Modulus | kg/mm² | 430 | 450 | 440 | 490 | 550 | 120 |
| Adhesion (Aluminum peel) | g/cm | 420 | 400 | 400 | 390 | 200 | 340 |
| Moisture absorption (72 hr) | % | 0.377 | 0.389 | 0.383 | 0.395 | 0.523 | 0.281 |
| Solder crack resistance | cracked samples | 1 | 2 | 1 | 1 | 6 | 10 |

Note: "←" means the same as left.

In Tables 4 and 5, the physical properties were evaluated by the following methods:

Gel time: 0.5 g of the mixture obtained in each of the Examples and Comparative Examples was placed in the concave portion of a hot plate at 180° C. and the time required until the mixture gelled was measured.

Glass transition temperature: Measured by use of a thermomechanical analysis apparatus (SHIMADZU DT-30).

Barcol hardness: Measured according to ASTM D-648 using Model 935 under the conditions of 175° C./3 minutes.

Flexural strength, flexural modulus: Measured according to JIS K-6911 using Instron type universal material tester (SHIMADZU IS-10T).

Moisture absorption: In a constant temperature constant moisture bath (TABAI PR-2), weight change was measured under the conditions of 85° C./85% RH.

Spiral flow: Measured according to EMMI-1-66 under the conditions of 175° C./70 kg/cm².

Adhesion (Aluminum peel): The mixture was transfer-molded on a commercially available aluminum foil, and peeling strength was measured.

Solder cracking resistance: Simulation IC (52 pins QFP package; package thickness: 2.05 mm) was subjected to moisture absorption under the conditions of 85° C./85% RH/72 hours, and immediately thereafter, immersed in a solder bath at 240° C. for 30 seconds, after which the number of IC samples in which crack was caused was determined. Ten test samples were used.

What is claimed is:

1. A thermosetting resin composition comprising, as the essential components, (a) an unsaturated imide compound represented by formula (1):

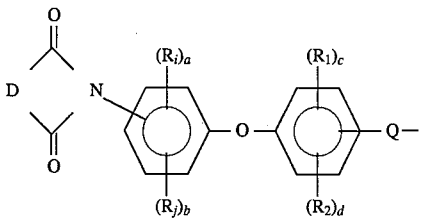

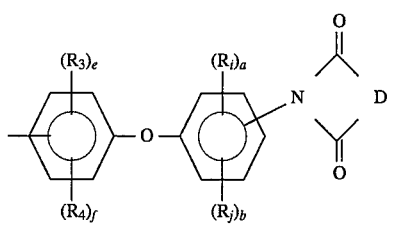

wherein Q represents an alicyclic structure-containing hydrocarbon having 4 to 20 carbon atoms; each of $R_1$, $R_2$, $R_3$, $R_4$, $R_i$ and $R_j$ represents a hydrogen atom, a halogen atom, a hydrocarbon group having 1–6 carbon atoms or a halogen-containing hydrocarbon group having 1–6 carbon atoms; and each of a, b, c, d, e and f represents an integer of 0–4 satisfying a+b≦4, c+d≦4 and e+f≦4; and D represents a divalent organic group having 2–24 carbon atoms and having an ethylenically unsaturated double bond, and (b) a curing accelerator.

2. A thermosetting composition according to claim 1, wherein Q is selected from the group consisting of:

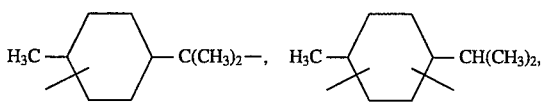

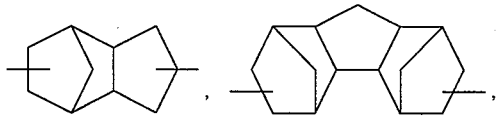

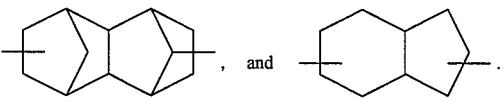

3. A thermosetting composition according to claim 1, wherein Q is

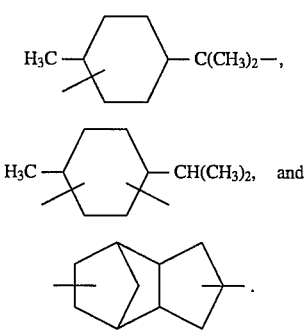

4. A thermosetting composition according to claim 1, wherein each of $R_1$, $R_2$, $R_3$, $R_4$, $R_i$ and $R_j$ represent a halogen atom.

5. A thermosetting composition according to claim 1, wherein each of $R_1$, $R_2$, $R_3$, $R_4$, $R_i$ and $R_j$ represent a hydrocarbon group having 1–6 carbon atoms.

6. A thermosetting composition according to claim 1, wherein each of $R_1$, $R_2$, $R_3$, $R_4$, $R_i$ and $R_j$ represent a halogentated hydrocarbon group having 1–6 carbon atoms.

7. A thermosetting composition according to claim 1, wherein each of $R_1$, $R_2$, $R_3$, $R_4$, $R_i$ and $R_j$ represent a cycloalkyl group having 3–6 carbon atoms or a phenyl group.

8. A thermosetting composition according to claim 1, wherein D is —CH=CH—, $CH_2$=CH—$CH_2$, —C($CH_3$)=CH—, or —C(Cl)=C(Cl)—.

9. A thermosetting resin composition comprising, as the essential components, (a) an unsaturated imide compound represented by formula (1):

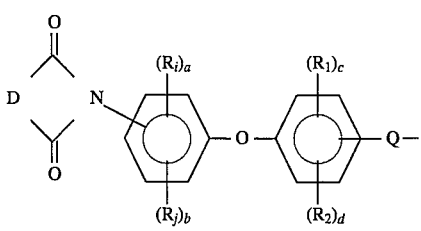

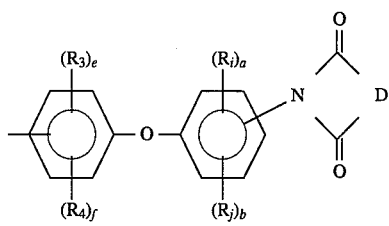

wherein Q represents an alicyclic structure-containing hydrocarbon having 4 to 20 carbon atoms; each of $R_1$, $R_2$, $R_3$, $R_4$, $R_i$ and $R_j$ represents a hydrogen atom, a halogen atom, a hydrocarbon group having 1–6 carbon atoms or a halogen-containing hydrocarbon group having 1–6 carbon atoms; and each of a, b, c, d, e and f represents an integer of 0–4 satisfying a+b≦4, c+d≦4 and e+f≦4; and D represents a divalent organic group having 2–24 carbon atoms and having an ethylenically unsaturated double bond, (b) a curing accelerator, (c) an epoxy resin and (d) an epoxy resin curing agent.

10. A thermosetting composition according to claim 9, wherein Q is selected from the group consisting of:

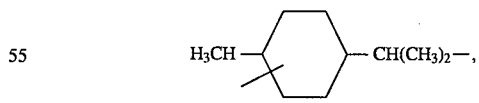

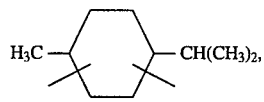

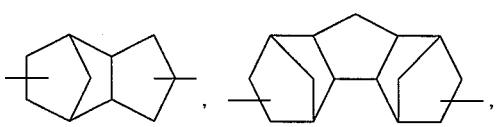

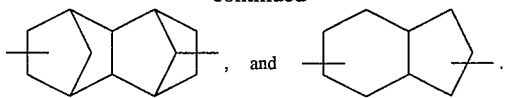, and

11. A thermosetting composition according to claim 9, wherein Q is

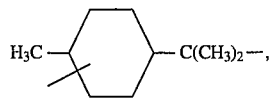

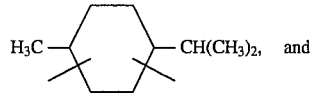 and

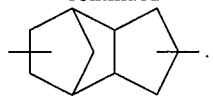.

12. A thermosetting composition according to claim 9, wherein each of $R_1$, $R_2$, $R_3$, $R_4$, $R_i$ and $R_j$ represent a halogen atom.

13. A thermosetting composition according to claim 9, wherein each of $R_1$, $R_2$, $R_3$, $R_4$, $R_i$ and $R_j$ represent a hydrocarbon group having 1–6 carbon atoms.

14. A thermosetting composition according to claim 9, wherein each of $R_1$, $R_2$, $R_3$, $R_4$, $R_i$ and $R_j$ represent a halogentated hydrocarbon group having 1–6 carbon atoms.

15. A thermosetting composition according to claim 9, wherein each of $R_1$, $R_2$, $R_3$, $R_4$, $R_i$ and $R_j$ represent a cycloalkyl group having 3–6 carbon atoms or a phenyl group.

* * * * *